US012569150B2

(12) United States Patent
Sweet, Jr. et al.

(10) Patent No.: US 12,569,150 B2
(45) Date of Patent: Mar. 10, 2026

(54) METHODS, DEVICES AND SYSTEMS FOR BIOPHYSICAL SENSING

(71) Applicant: Cypress Semiconductor Corporation, San Jose, CA (US)

(72) Inventors: Richard Sweet, Jr., San Diego, CA (US); Igor Kolych, Lviv (UA); Adrian Mikolajczak, Los Altos, CA (US)

(73) Assignee: Infineon Technologies Americas Corp., El Segundo, CA (US)

( * ) Notice: Subject to any disclaimer, the term of this patent is extended or adjusted under 35 U.S.C. 154(b) by 880 days.

(21) Appl. No.: 17/591,103

(22) Filed: Feb. 2, 2022

(65) Prior Publication Data

US 2023/0113396 A1     Apr. 13, 2023

Related U.S. Application Data

(60) Provisional application No. 63/255,372, filed on Oct. 13, 2021.

(51) Int. Cl.
*A61B 5/021*     (2006.01)
*A61B 5/00*     (2006.01)
(Continued)

(52) U.S. Cl.
CPC ...... *A61B 5/02108* (2013.01); *A61B 5/02427* (2013.01); *A61B 5/0507* (2013.01); *A61B 5/11* (2013.01); *A61B 5/277* (2021.01); *A61B 5/6824* (2013.01); *A61B 5/6831* (2013.01); *A61B 5/721* (2013.01); *A61B 2560/0209* (2013.01); *A61B 2562/046* (2013.01)

(58) Field of Classification Search
CPC ............ A61B 5/02108; A61B 5/02427; A61B 5/0507; A61B 5/11; A61B 5/277; A61B 5/6824; A61B 5/6831; A61B 5/721; A61B 2560/0209; A61B 2562/046; A61B 5/02125; A61B 5/1126; A61B 2560/0223; A61B 2562/0214; A61B 2562/0219; A61B 5/0082; A61B 2562/164; A61B 2562/166; A61B 5/6833; G01S 7/003; G01S 13/88; G01S 17/88; G01S 7/028; G01S 7/032; G01S 13/86; G01S 17/89
See application file for complete search history.

(56) References Cited

U.S. PATENT DOCUMENTS 9,462,979 B2 * 10/2016 Lisogurski ........... A61B 5/6826
2013/0274565 A1 * 10/2013 Langer .................. A61B 5/318
600/595

(Continued)

*Primary Examiner* — Eric F Winakur
*Assistant Examiner* — Noah M Healy

(57) ABSTRACT

A method can include attaching a sensor device contained in a sensor structure to a body; sensing motion of the body with at least one motion capacitive sensor of the sensor device that senses a capacitance change resulting from a difference in orientation of the motion capacitive sensor and a surface of the body. If motion of the body is not sensed with the motion capacitive sensor, sensor readings can be acquired with a biophysical sensor that emits signals into a portion of the body below the sensor structure, and generate data for a feature of the body with the sensor readings. If motion of the body is not sensed with the motion capacitive sensor, data for the feature of the body is not generated. Related devices and systems are also disclosed.

14 Claims, 16 Drawing Sheets

(51) Int. Cl.
    *A61B 5/024*           (2006.01)
    *A61B 5/0507*         (2021.01)
    *A61B 5/11*            (2006.01)
    *A61B 5/277*          (2021.01)

(56)             References Cited

U.S. PATENT DOCUMENTS

| | | | |
|---|---|---|---|
| 2017/0095215 A1* | 4/2017 | Watson | A61B 5/0002 |
| 2018/0353086 A1* | 12/2018 | Turner | G01S 13/50 |
| 2019/0069786 A1* | 3/2019 | Perez-Camargo | A61B 5/0205 |
| 2022/0167857 A1* | 6/2022 | Lin | G16H 40/63 |

* cited by examiner

CAP MOTION DETECT
412A

CAP MOTION DETECT
412B

CAP MOTION DETECT
412C

SAMPLE OUT   564
CAP MOTION DETECT   512

COUNT OUT   664
CAP MOTION DETECT
612

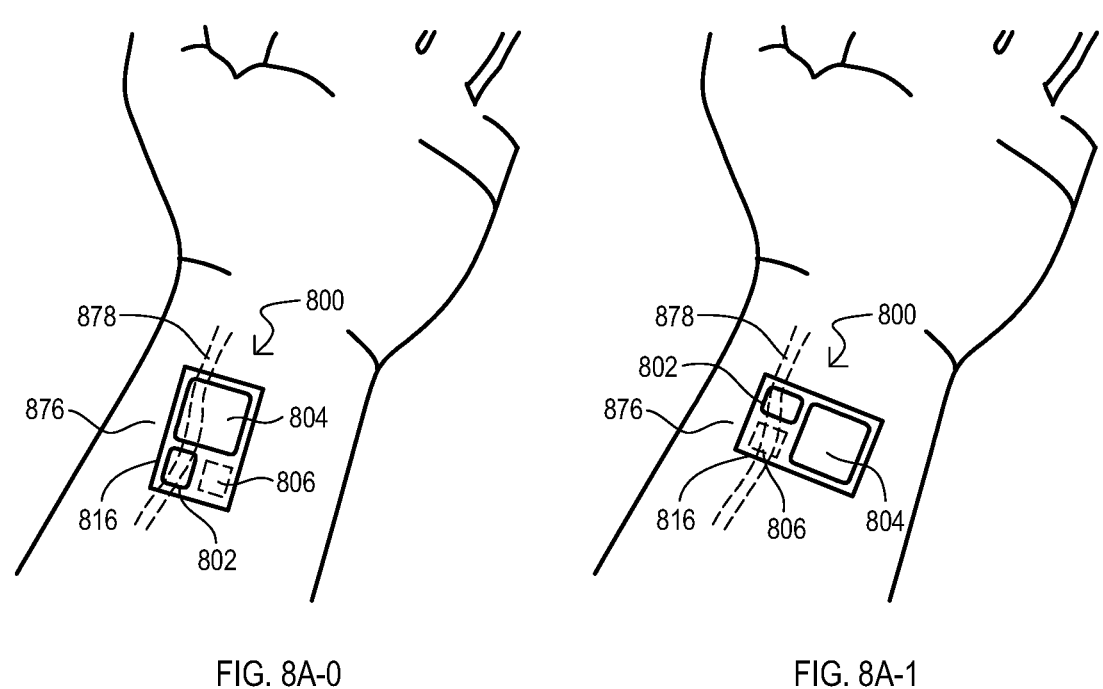
FIG. 8A-0                                    FIG. 8A-1
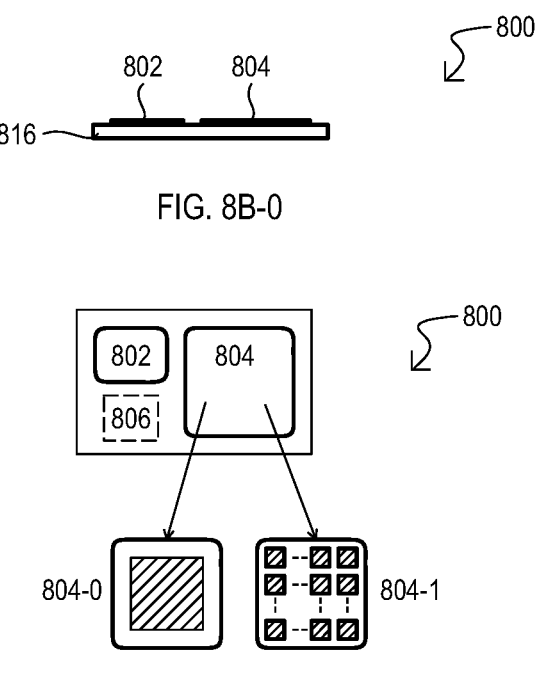
FIG. 8B-0
FIG. 8B-1

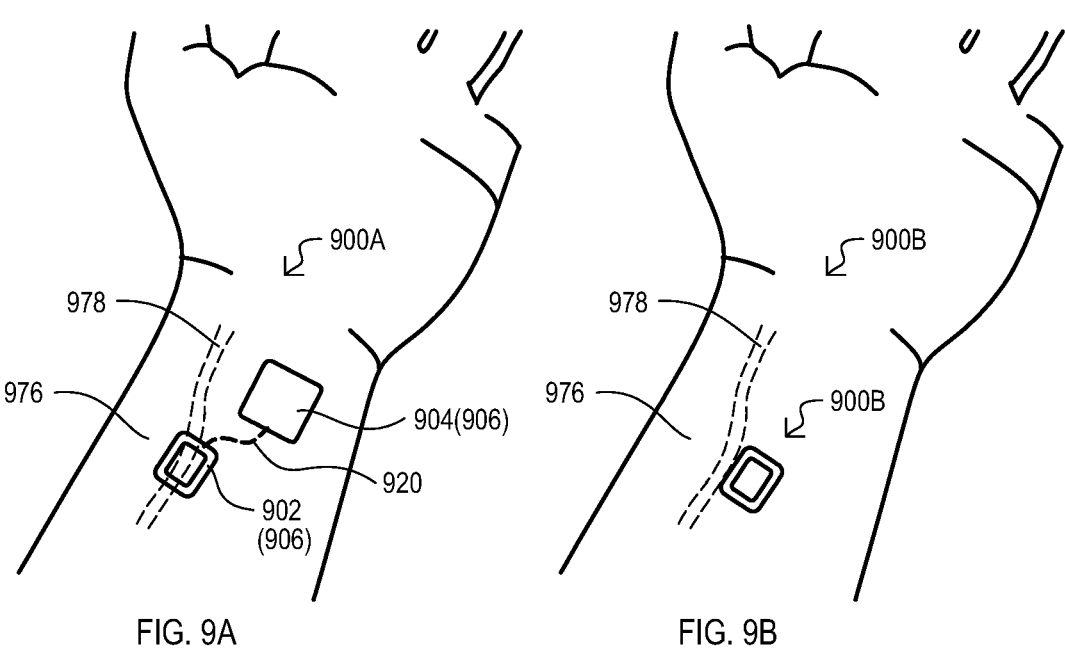
FIG. 9A                    FIG. 9B
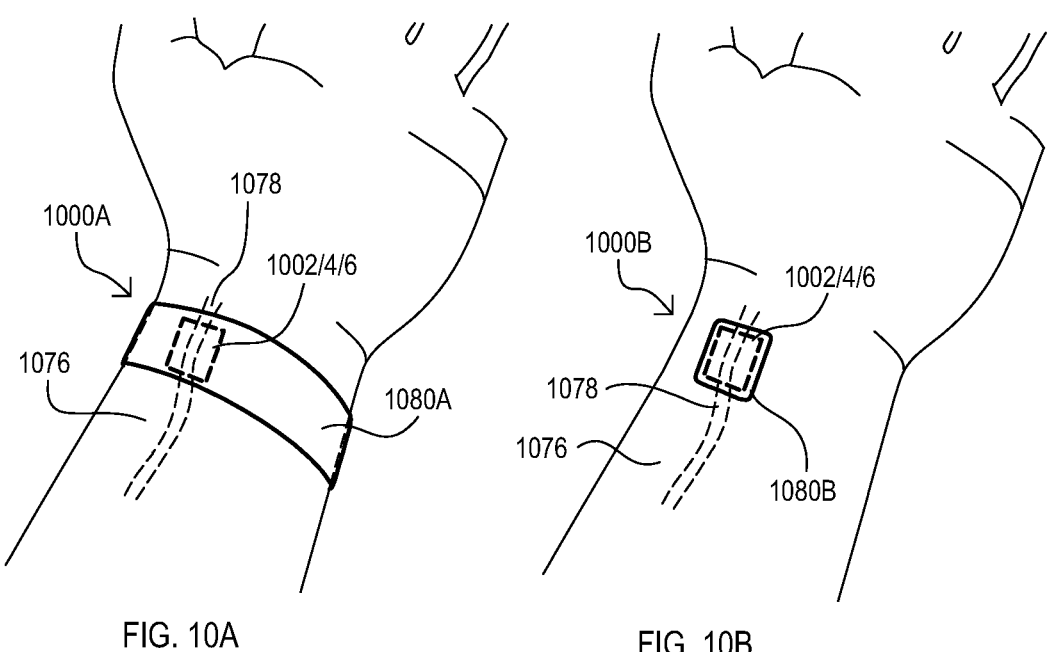
FIG. 10A                   FIG. 10B

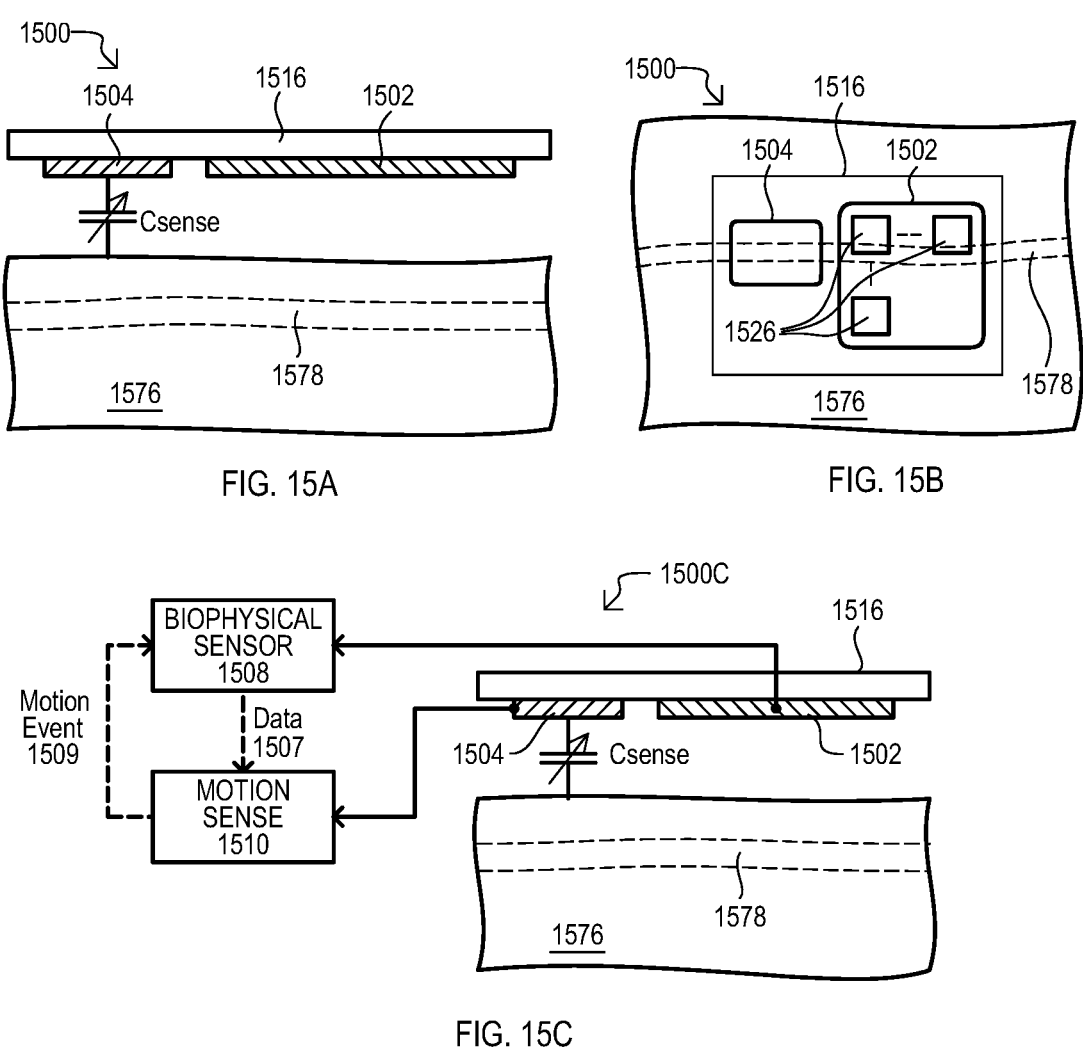
FIG. 15A
FIG. 15B
FIG. 15C
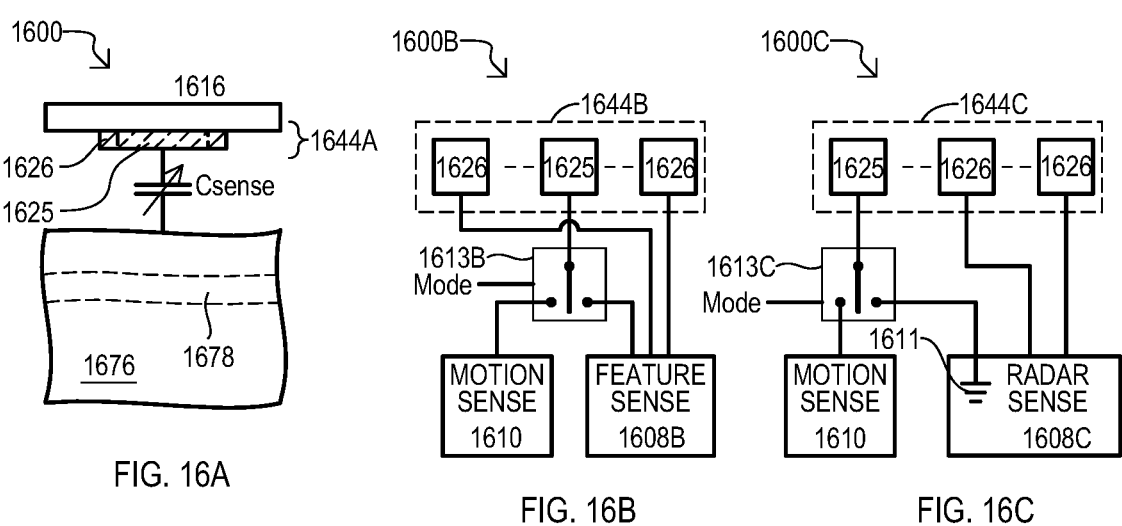
FIG. 16A
FIG. 16B
FIG. 16C

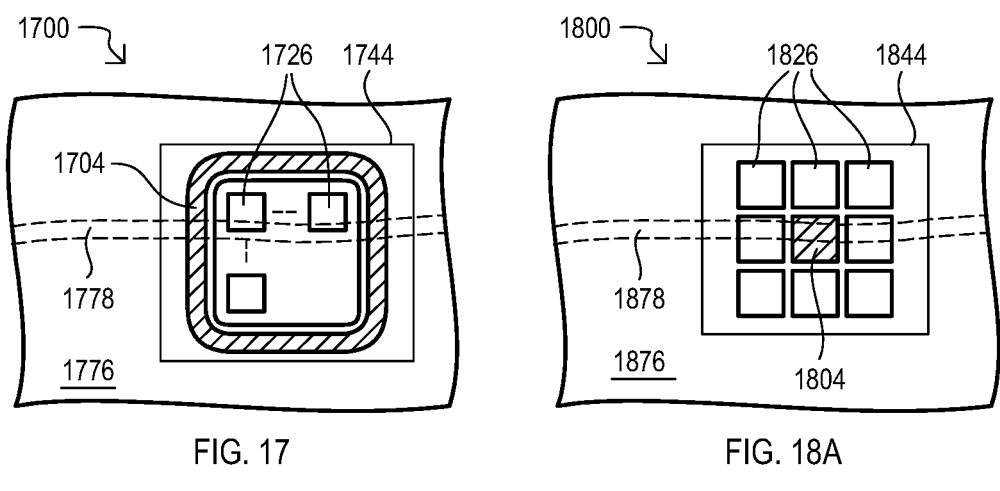
FIG. 17
FIG. 18A
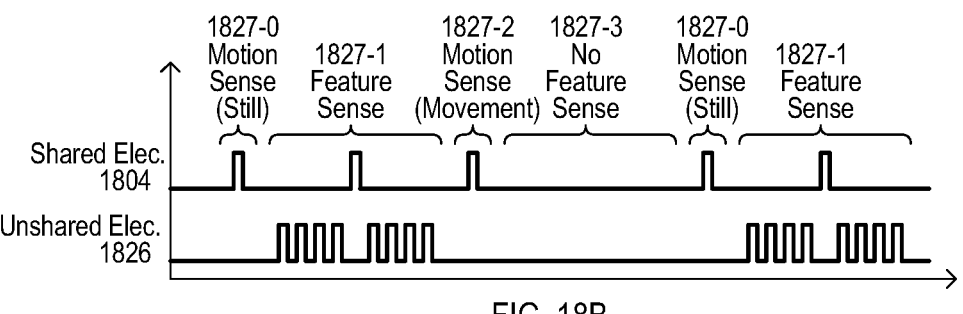
FIG. 18B
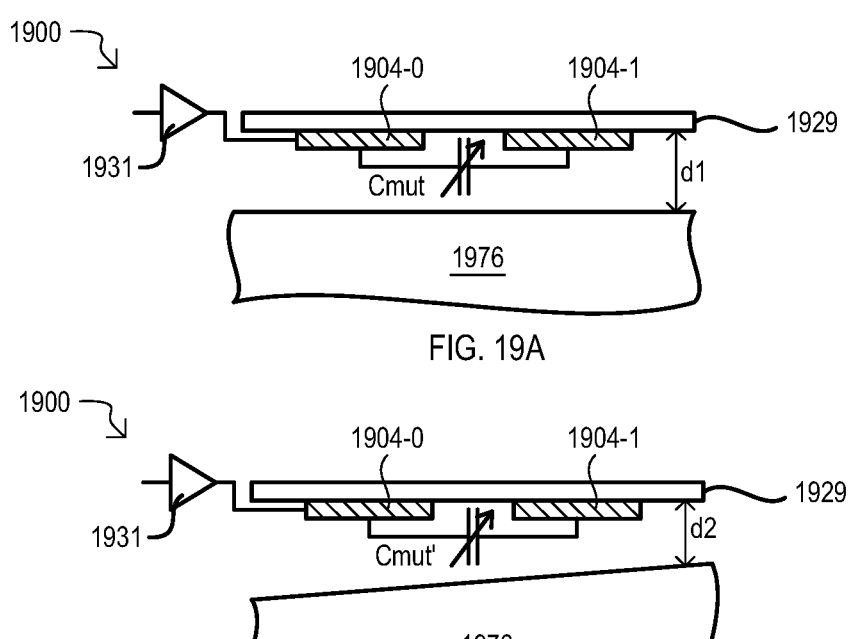
FIG. 19A
FIG. 19B

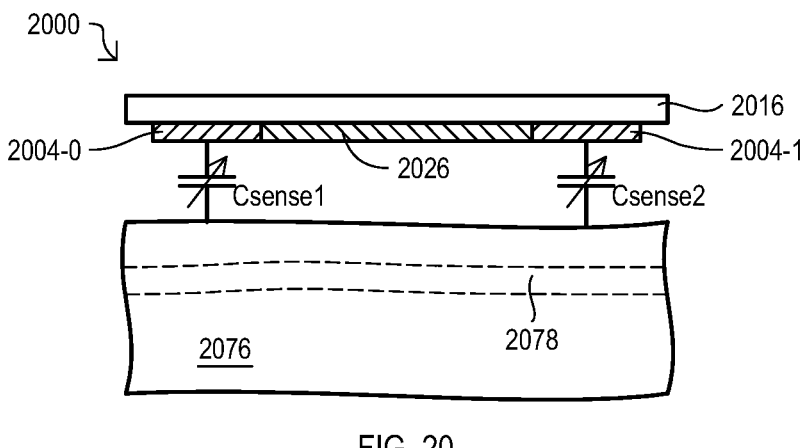
FIG. 20
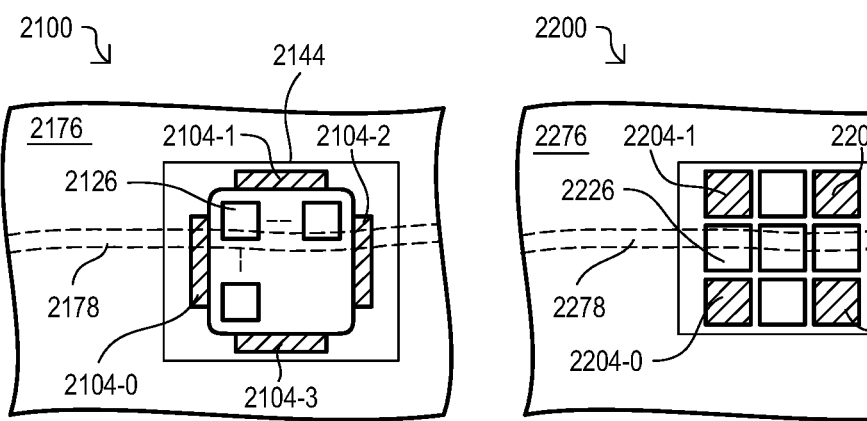
FIG. 21                    FIG. 22
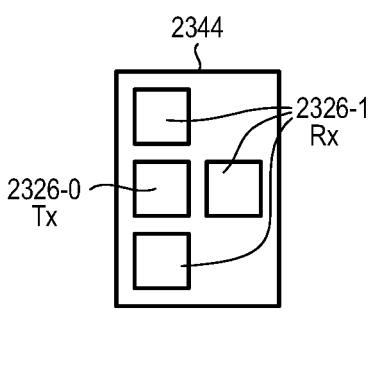
FIG. 23
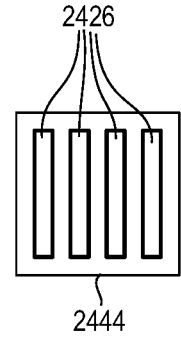
FIG. 24

METHODS, DEVICES AND SYSTEMS FOR BIOPHYSICAL SENSING

CROSS-REFERENCE TO RELATED APPLICATION

This application claims the benefit of U.S. Provisional Application No. 63/255,372 filed on Oct. 13, 2021, which is incorporated herein by reference in its entirety.

TECHNICAL FIELD

The present disclosure relates generally to biophysical sensors, and more particularly to biophysical sensors that can be affected by movement of a monitored subject.

BACKGROUND

Biophysical sensors can measure one or more biological features of a subject, typically in a healthcare setting. However, some measurements can be affected by movement of the subject, or are to be performed while the subject is still. As but one of many possible examples, an arterial pressure waveform (APW) can be used for vital sign estimations. APW values can be derived with biophysical sensors that employ various sensing techniques, including radar, optical sensing (e.g., photoplethysmography, PPG) and capacitance sensing. APW can be measured at many locations of the human body, including certain regions of the limbs. However, conventional APW readings are made relative to a skin surface. As a result, readings taken while a subject is moving can introduce motion artifacts. While some motion artifacts can be reduced or removed with signal filtering, such filtering can also remove morphology important for accurate vial sign estimations.

Consequently, conventional APW measurements, like other measurements such a blood pressure, are taken while a subject is still, or involve repeated measurements in the event a subject moves while undergoing measurement or have reduced fidelity due to filtering of motion artifacts.

SUMMARY

Embodiments can include a method that senses motion of a body with one or more capacitance sensors. If motion of the body is sensed with a capacitance sensor, a biophysical sensor can be placed in a sleep mode in which the biophysical sensor does not take the sensor readings of the body. If motion of the body is not sensed, the biophysical sensor can be placed into a sense mode in which the biophysical sensor takes sensor readings of the body. The biophysical sensor can be proximate to a surface of the body.

BRIEF DESCRIPTION OF THE DRAWINGS

FIGS. 8A-0 to 8B-1 are diagrams showing a sensor system according to additional embodiments.

FIGS. 9A and 9B are diagrams showing a sensor system according to another embodiment.

FIGS. 10A and 10B are diagrams showing wearable systems according to embodiments.

FIGS. 15A and 15B are diagrams showing a sensor system according to another embodiment. FIG. 15C is a diagram of a sensor system according to an embodiment.

FIG. 16A is a diagram showing self-capacitance sensing that can be included in embodiments. FIGS. 16B and 16C are diagrams showing of systems in which an electrode can be shared between motion sensing and feature sensing.

FIG. 17 is a diagram of a system having a surrounding capacitance sensor electrode according to an embodiment.

FIGS. 18A and 18B is a diagram showing a system having an array of capacitance sensing electrodes in which one or more electrodes can sense motion as well as a body feature.

FIGS. 19A and 19B are diagrams showing mutual capacitance sensing that can be included in embodiments.

FIG. 20 is a diagram showing motion sensing with capacitance sensing at opposing edges of device according to an embodiment.

FIG. 21 is a diagram of a system having motion capacitance sensing at opposing edges of a feature sensing electrode array.

FIG. 22 is a diagram of a system having motion capacitance sensing with electrodes at ends of a sensing electrode array.

FIG. 23 is a diagram of a radar sensing electrode array that can be included in embodiments.

FIG. 24 is a diagram of a sensing electrode array that can be included in embodiments.

DETAILED DESCRIPTION

According to embodiments, a sensor system can include feature sensors, which can detect a feature of a body (e.g., artery movement, dimensions, pressure) and a capacitive sensor which can detect movement of the body. If a capacitive sensing indicates that the body/limb is still, a biophysical sensor can be placed into a sense mode to take readings that could otherwise be adversely affected by movement of the body/limb. If capacitance sending indicates that the body/limb is moving, a biophysical sensor can be placed into a sleep mode in which it may not take readings and/or readings are not used to determine characteristics of a body feature.

Embodiments can include biophysical sensors that are switched between sense and sleep modes of any suitable sensor type, including radar sensors, optical sensors and capacitance sensors. Such sensors can separate from, or the same as, those used for capacitive motion sensing. Optical sensors can include, but are not limited to photoplethysmography (PPG) sensors.

Embodiments can generate values for a biological reading of any suitable type, including but not limited to: arterial position, arterial pressure waveforms (APWs), blood pressure (BP) and/or arterial dimensions. Arterial dimensions can be used in the measurement or estimation of pulse transmit time (PTT) and/or pulse wave velocity (PWV).

Capacitive motion sensing can use self-capacitance and/or mutual capacitance to sense motion.

Figure 1:
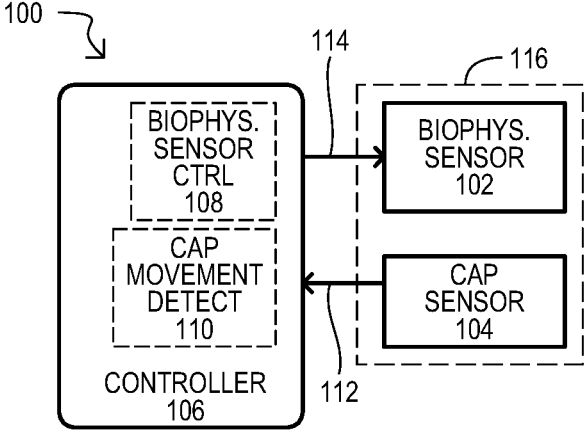
FIG. 1 is a block diagram of a system according to an embodiment.

FIG. 1 is a block diagram of a system 100 according to an embodiment. A system 100 can include a biophysical sensor 102, a capacitance sensor 104 and a controller 106. A biophysical sensor 102 can sense a biological feature of a body, and in some embodiments, can be used in a measurement operation that is sensitive to movement. A biophysical sensor 102 can use any suitable mechanism for sensing, including but not limited to: radar, light (e.g., imaging) or capacitance. A biophysical sensor 102 can have at least two modes of operation, including a sense mode, in which sensor readings can be taken, and a sleep mode, in which sensor readings are not taken or are ignored. In some embodiments, a sleep mode can consume less energy than a sense mode.

A capacitance sensor 104 can generate variations in capacitance in response to movement of the sensor with respect to a body. A capacitance sensor 104 can take any suitable form according to the type of motion to be sensed. A capacitance sensor 104 can include any number of sensor plates, from a single sense plate to multiple sense plates, including an array of capacitance sensors. A capacitance sensor 104 can utilize self-capacitance of one or more sensor electrodes, or mutual capacitance between electrodes to detect movement (i.e., motion). Capacitance sensor 104 can provide movement indications 112 to a controller 106.

In the embodiment shown, a controller 106 can execute sensor control 108 and movement detection 110. Sensor control 108 can control a mode of biophysical sensor 102 in response to movement detected by movement detection 110. Movement detection 110 can analyze movement sensor indications 112 to determine if movement has taken place. In alternate embodiments, such analysis can take place in the capacitance sensor 104, and a capacitance sensor 104 can provide a movement indication or the like. Based on movement indications generated by movement detection 110, sensor control 108 can use mode control 114 to place biophysical sensor 102 into a sense mode or a sleep mode. In alternate embodiments, sensor control 108 can be part of biophysical sensor 102.

In some embodiments, a biophysical sensor 102 and capacitance sensor 104 can be designed to attach to, or be positioned proximate to, a surface of a body, such as the skin of a person. In some embodiments, a biophysical sensor 102 can be a separate device from a capacitance sensor 104. In other embodiments, biophysical sensor 102 and capacitance sensor 104 can be situated in a same sensor body (i.e., structure) 116 to provide a fusion sensor that combines the two sensor types.

In this way, a biophysical sensor that can be sensitive to movement can be placed in a sleep mode when movement is detected and placed in a sense mode when movement is not detected (i.e., a sensed body is still). Such an arrangement can provide more accurate readings, as movement artifacts are not present in biophysical sensor readings; can reduce power, as a sleep mode can consume less power than a sense mode; and present a less intrusive sensing regime as measurements can be taken when a subject is still of its own accord, instead forcing a subject to be still.

While embodiments disclosed herein can include one biophysical sensor, alternate embodiments can include multiple biophysical sensors, including biophysical sensors of different types.

Figure 2:
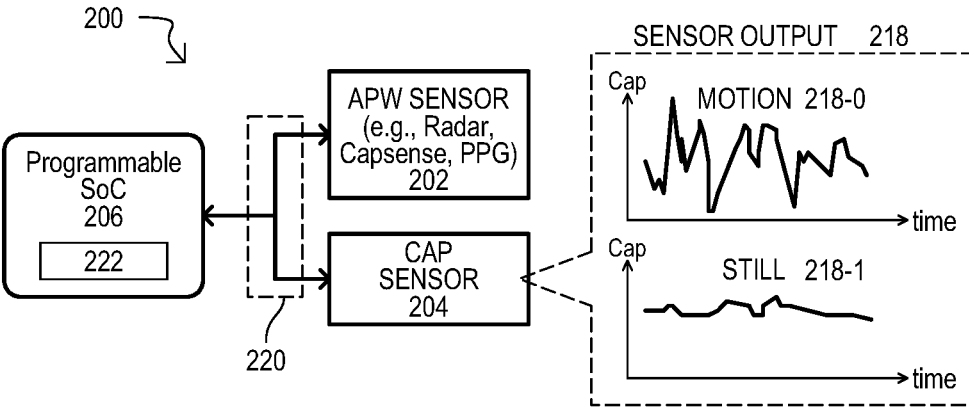
FIG. 2 is a block diagram of an arterial pressure sensor system according to an embodiment.

FIG. 2 is a block diagram of a system 200 according to another embodiment. A system 200 can include an APW sensor 202, capacitance sensor 204, programmable system-on-chip (SoC) 206, and communication path 220. A capacitance sensor 204 can sense motion as described herein and equivalents. In the embodiment shown, capacitance sensor 204 can provide a sensor output 218 that varies depending upon whether a sensed body is in motion 218-0 or is still 218-1. A capacitance sensor 204 can provide sensor outputs to SoC 206 over communication path 220. Communication path 220 can be a wired communication path, wireless communication path, or combination thereof.

APW sensor 202 can generate sensor data for an APW reading. APW sensor 202 can include any suitable sensor type, including but not limited to radar, capacitance sensing, or a PPG type sensor. APW sensor 202 can provide sensor data over communication path 220 to SoC 206.

SoC 206 can include one or more processors and associated memory for executing system functions, including placing APW sensor 202 into a sleep mode upon sensing motion with capacitance sensor 204, and then returning APW sensor 202 to a sense mode when capacitance sensor 204 indicates stillness. In some embodiments, SoC 206 can include signal processing circuits 222 for analyzing sensor data from APW sensor 202 and/or capacitance sensor 204. In some embodiments, SoC 206 can sense motion from sensor output 216 from capacitance sensor 204. In some embodiments, SoC 206 can generate data for an APW from sensor data received from APW sensor 202.

In this way, a system can provide sensor data for an APW without the need for added filtering that removes motion artifacts, which can remove valuable features of the APW and/or consume more power.

Figure 3:
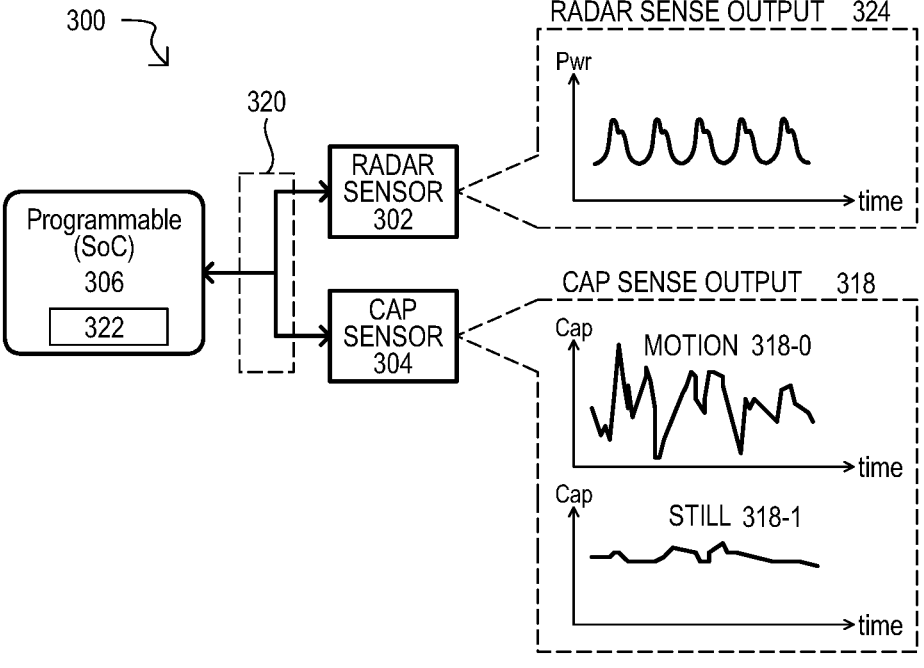
FIG. 3 is a block diagram of a radar sensor system according to an embodiment.

FIG. 3 is a block diagram of a system 300 according to another embodiment. A system 300 can include a radar sensor 302, capacitance sensor 304, programmable system-on-chip (SoC) 306, and communication path 320. A capacitance sensor 304 can sense motion as described for FIG. 2 or an equivalent.

A radar sensor 302 can emit radar signals into a body and sense returned signals. From such signals, a radar sensor 302 can detect biological features of a subject. In some embodiments, a radar sensor 302 can be used to generate an APW. However, this should not be construed as limiting. Alternate embodiments can use radar sensing for any other suitable biophysical reading, including but not limited to other aspects of the circulatory system or other system of a body.

A radar sensor 302 and capacitance sensor 304 can be in communication with SoC 306 over communication path 320 as described for other embodiments herein. SoC 306 can place radar sensor 302 into sense and sleep modes in response to motion sensed by capacitance sensor 304. SoC 306 can include signal processing circuits 322 which can analyze sensor data from radar sensor 302 and/or capacitance sensor 304.

In this way, a system can selectively enable or disable a radar sensor based on subject movement. This can provide substantial power savings, and enable radar sensing to be deployed in portable devices, such as wearable devices.

Figure 4A:
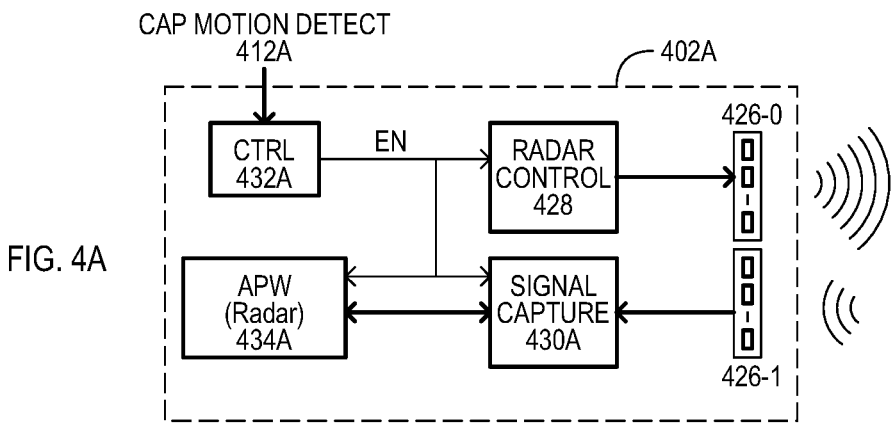
FIGS. 4A to 4C are block diagrams showing sensor systems according to embodiment.
Figure 4B:
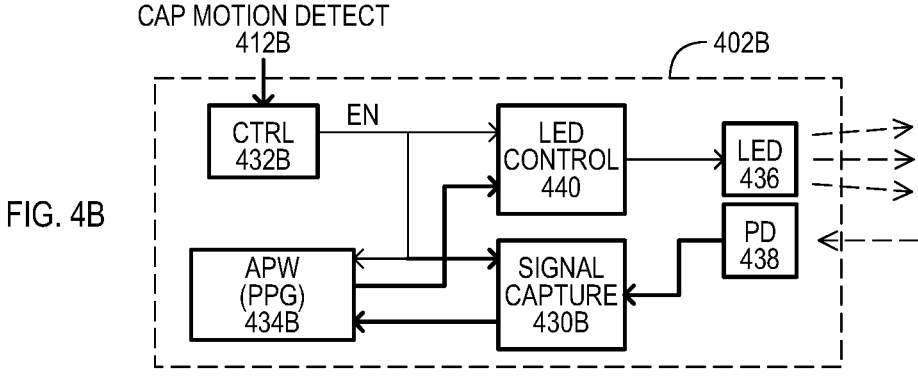
Figure 4C:
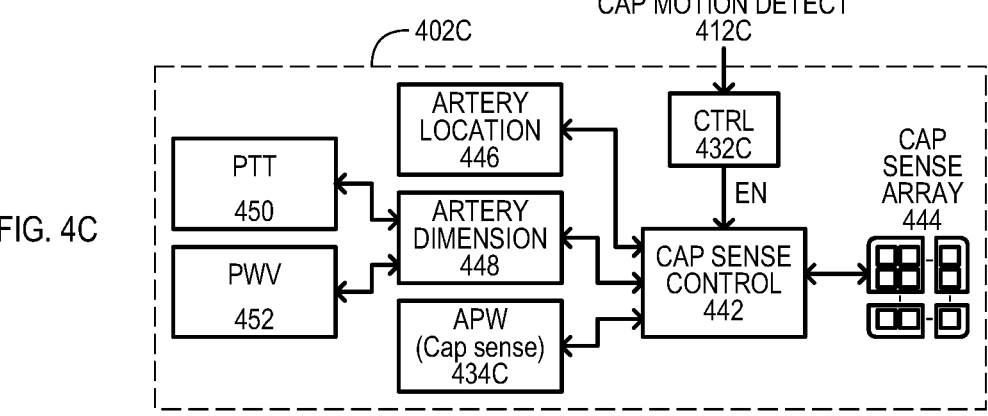

FIGS. 4A to 4C are diagrams of sensor systems that can be included in embodiments. FIG. 4A shows a radar sensor system 402A that can include a transmitting (Tx) antenna 426-0, receiving (Rx) antenna 426-1, radar control circuits 428, signal capture circuits 430A, APW processing circuits 434A and control circuits 432A. Radar control circuits 428 can control the transmission of radar signals by Tx antenna 426-0 in a sense operation. Signal capture circuits 430A can capture return signals received on Rx antenna 426-1. APW processing circuits 434A can process received radar captures to create an APW. Control circuits 432A can enable or disable any or all portions of sensor system 402A in response to a motion detect indication 412A. A motion detect indication 412A received by system 420A can be generated from a capacitance sensor as described herein and equivalents.

FIG. 4B shows an optical sensing system 402B that can include a light source 436, a light detector 438, illumination control circuits 440, signal capture circuits 430B, APW processing circuits 434B and control circuits 432B. A light source 436 can include any suitable light source, including one or more LEDs. A light detector 438 can be any suitable photosensor, including one or more photodiodes and/or phototransistors. LED control circuits 440 can control the emission of light. Signal capture circuits 430B can capture signals generated by light detector 438. APW processing circuits 434B can process received light capture signals to create an APW. Control circuits 432B can enable or disable any or all portions of sensor system 402B in response to a motion detect indication 412B, which can be generated as described for embodiments herein.

FIG. 4C shows a capacitance sensing system 402C that can include a capacitance sense array 444, capacitance sense control circuit 442, and control circuits 432C. A capacitance sense array 444 can include multiple capacitance sensors which can be scanned for capacitance according to a desired sensing operation. Capacitance sense control circuit 442 can control capacitance sense array 444 according to a type of capacitance sensing operation. A capacitance sensing operation can include self-capacitance sensing and/or mutual capacitance sensing.

According to embodiments, a capacitance sensing system 402C can perform any number of artery measurement functions. Such measurement functions can include any of: artery location analysis circuits 446, artery dimension analysis circuits 448 and APW processing circuits 434C. Artery location analysis circuits 446 can utilize capacitance sensing of capacitance sense array 444 to locate the position of an artery 446. APW processing circuits 434C can utilize capacitance sensing of sense array 444 to generate an APW. Artery dimension analysis circuits 448 can determine dimensions of an artery utilizing capacitance sensing with capacitance sense array 444. From artery dimensions, PTT analysis circuits 450 can determine a PTT for the artery and/or PWV analysis circuits 452 can determine a PWV for the artery. Control circuits 432C can enable or disable any or all portions of sensor system 402C in response to a motion detect indication 412C, which can be as described herein. As will be described for later embodiments herein, in other embodiments, all or a portion of a capacitance sense array 444 can be used for motion sensing.

Systems shown in FIGS. 4A to 4C can be single devices (e.g., IC devices) or can be distributed over multiple devices. As but a few of many possible examples, circuits that generate waveforms (APW processing circuits 434A, 434B, 434C; artery location circuits 446; artery dimension circuits 448; PTT analysis circuits; or PWV analysis circuits) can be firmware and/or software executed by a processor on another device separate from those that include sensors.

In this way, capacitance sensing motion can be used to control radar, optical or other capacitance sensing systems, to avoid motion induced error/artifacts, reduce power consumption.

Figure 5:
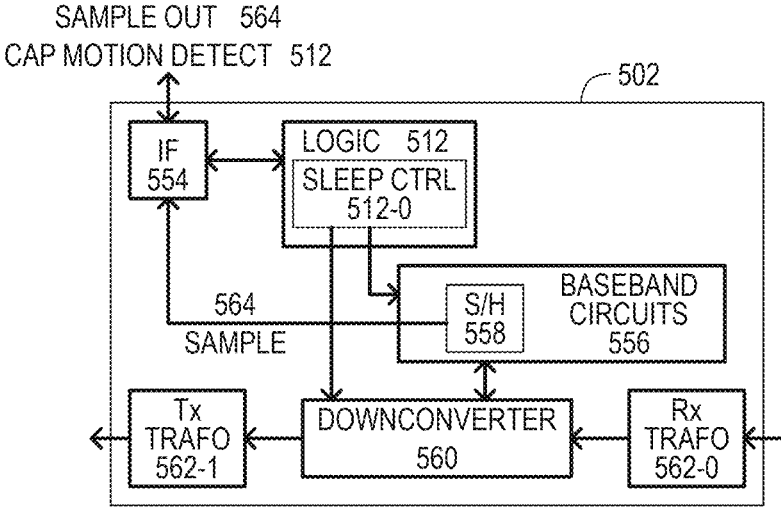
FIG. 5 is a block schematic diagram of a radar integrated circuit (IC) device that can be included in embodiments.

FIG. 5 is a block diagram of a radar integrated circuit (IC) device 502 according to an embodiment. A radar IC device 502 can be formed in a single IC package. In some embodiments, a radar IC device 502 can be formed with a single IC substrate. A radar IC device 502 can include interface (IF) circuits 554, logic circuits 512, baseband circuits 556, downconverter circuits 560, Rx radar transformer (trafo) 562-0 and Tx trafo 562-1. Rx trafo 562-0 can detect return radar signals from one or more antennas to derive a biophysical measurement. Tx trafo 562-1 can generate radar signals for transmission into a body to generate return radar signals. Downconverter circuits 560 can convert between radar signals frequencies and a lower baseband frequency. Baseband circuits 556 can receive downconverted signals, and can include sample and hold (S/H) circuits 558 for sampling a processed radar return signal.

Logic circuits 512 can control operations of a radar IC device 502. Logic circuits 512 can include sleep control functions 512-0 which can switch radar IC device 502 between sleep and sense modes in response to a capacitance motion detection indication 512, as described herein. IF circuits 554 can receive capacitance motion detection indication 512 and provide sampled values 564 as an output.

Figure 6:
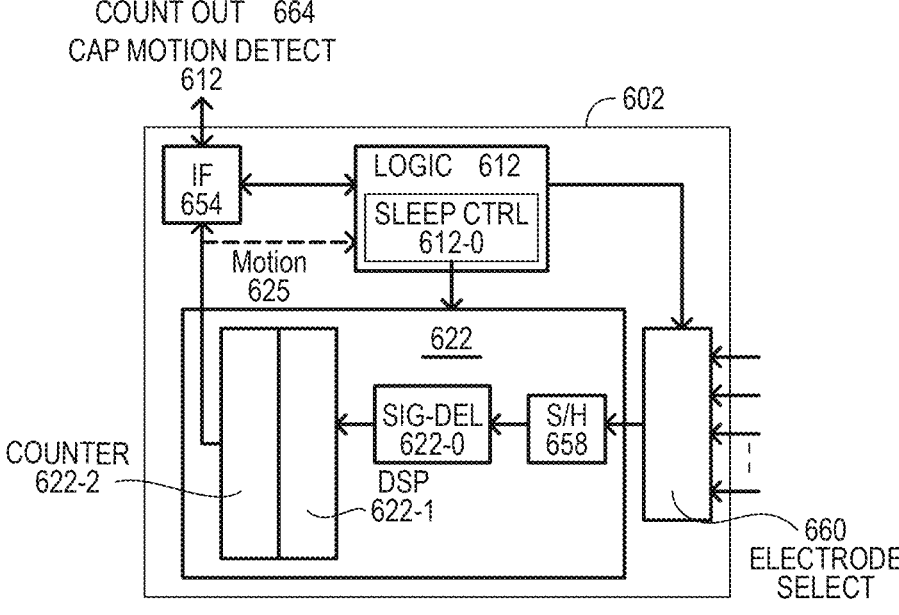
FIG. 6 is a block schematic diagram of a capacitance IC device that can be included in embodiments.

FIG. 6 is a block diagram of a capacitance sense (cap sense) IC device 602 according to an embodiment. A cap sense IC device 602 can be formed in a single IC package, and in some embodiments, with a single IC substrate. A cap sense IC device 602 can include IF circuits 654, logic circuits 612, signal processing circuits 622, and electrode selection circuits 660. Electrode selection circuits 660 can select capacitance sense electrodes, from a capacitance electrode array, for example. Signal processing circuits 622 can include a S/H section 658, a sigma-delta modulator section 622-0, a digital signal processing (DSP) section 622-1, a counter 622-2 and an evaluation section. S/H section 658 can sample current and/or voltage induced on an electrode 658. Sigma-delta modulator section 622-0 can modulate the sampled signal into a bit stream. DSP 622-1 can perform digital filtering and any other suitable signal processing on the generated bit stream. A counter 622-2 can generate a count value from a processed bit stream that can representing a capacitance present at a sampled electrode (or between electrodes). Such a count value 664 can be output at IF circuits 654. While FIG. 6 shows a cap sense IC device 602 that utilizes sigma-delta modulation, this should not be construed as limiting. Alternate embodiments can use any other suitable analog-to-digital conversion technique.

Logic circuits 612 can control operations of a cap sense IC device 602, and can include sleep control functions 612-0 which can switch cap sense IC device 602 between sleep and sense modes in response to a capacitance motion detection indication 612, as described herein. IF circuits 664 can receive capacitance motion detection indication 612 and provide count output values 664.

In some embodiments, capacitance sensing operations, in addition to sensing a body feature (e.g., APW), can execute motion sensing. In such an embodiment, motion sensing capacitance values 625 can be provided to logic 612, which can sense motion from such values.

In this way, systems can include a radar or cap sense IC device which can provide and advantageously small physical footprint, as well as reduced power consumption for wearable devices, or the like.

Figure 7:
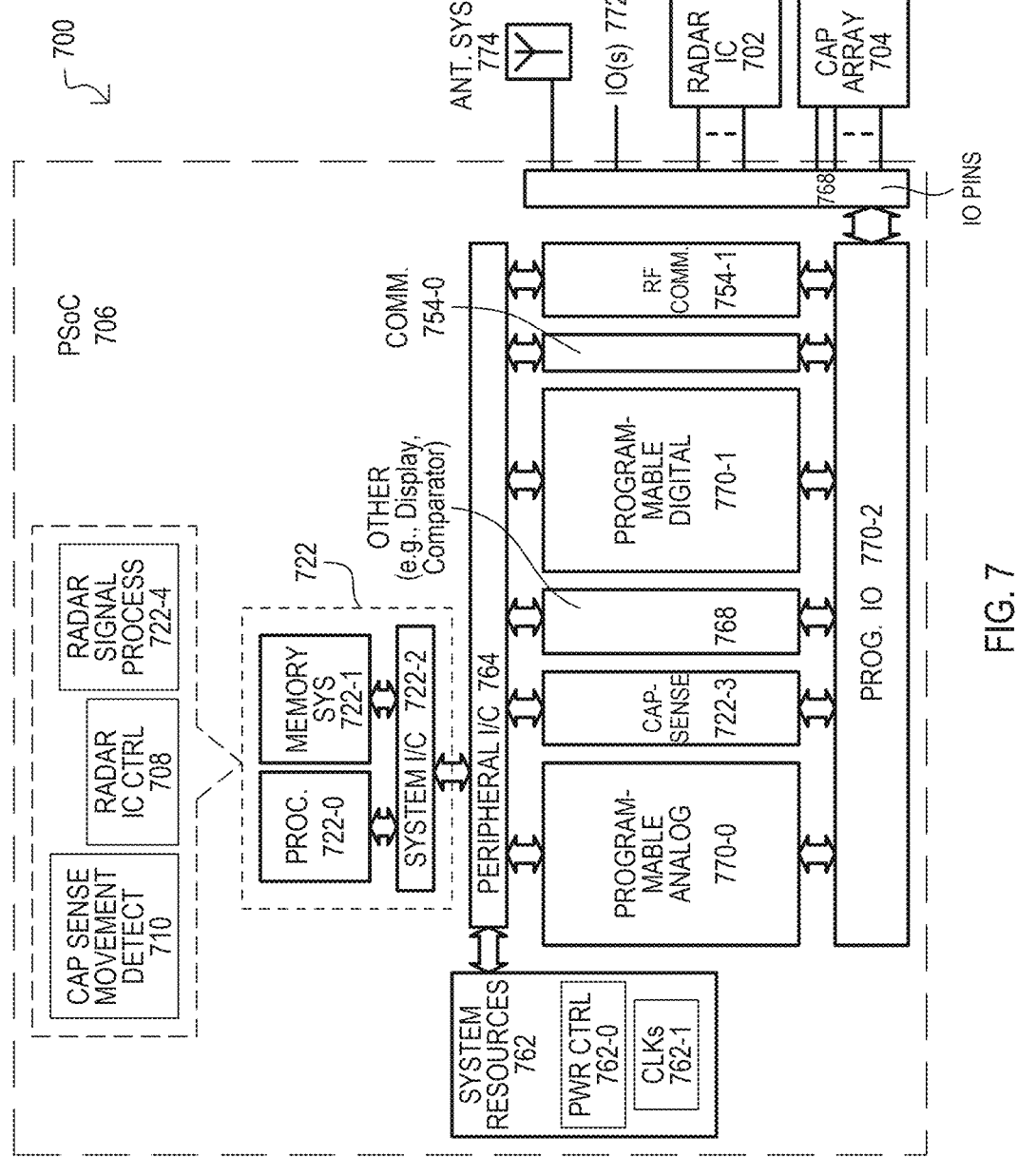
FIG. 7 is a block diagram of a sensor system that includes a programmable system-on-chip (SoC), according to an embodiment.

FIG. 7 shows a system 700 according to a further embodiment. A system 700 can include a radar IC device 702, capacitance array 704, and programmable SoC 706. A radar IC device 702 and capacitance array 704 can take the form of any of those described herein or equivalents.

Programmable SoC 706 can include processing circuits 722, system resources 762, peripheral interconnect 764, programmable analog circuits 770-0, capacitance sense circuits 722-3, other fixed circuits 768, programmable digital circuits 770-1, communication circuits 754-0, RF communication circuits 754-1, programmable IOs 770-2, and IO pins 768. Processing circuits 722 can include a processor section 722-0 and memory section 722-1 connected to one another by a system interconnect 722-2. Processor section 722-0 can include one or more processors. A memory section 722-1 can include one or more memory circuits, including volatile and/or nonvolatile memory circuits. In some embodiments, a memory section 722-1 can include instructions executable by processor section 722-0 to provide various functions. Such functions can include, but are not limited to capacitance movement detection 710, radar IC control 708 and radar signal processing 722-4. Capacitance movement detection 710 can sense movement by processing capacitance values received from capacitance array 704. Radar IC control 708 can control radar IC device 702, including placing the device in sense or sleep modes. Radar signal processing 722-4 can process radar signals to generate a biological reading, including but not limited to an APW.

System resources 762 can provide or control various system resources of the SoC 706, and can include power control 762-0 and timing clocks 762-1. Peripheral I/C 764 can enable connection between processing circuits 722 and other sections of the device. Programmable analog circuits 770-0 can include programmable circuit elements that can be configured with configuration data. Capacitance sense circuits 722-3 can be connected to capacitance sense array 704 via programmable IO 770-2, and can execute capacitance sense functions with the capacitance sense array 704. Other fixed circuits 768 can include circuits having various fixed functions, including but not limited to display drivers and analog comparators.

Programmable digital circuits 770-1 can include digital circuits configurable by configuration data. In some embodiments, programmable digital circuits 770-1 can include, or be configured into, digital filters and/or counters that can be included in capacitance sensing operations and/or the processing of data samples provided by radar IC device 702. Communication circuits 754-0 can enable communications with the system 700, and can include any suitable interface, including one or more serial interfaces. Communication circuits 754-0 can be connected to IOs 772 through programmable IO 770-2. RF communication circuits 754-1 can enable wireless communications with the system 700 according to one or more wireless protocols, including but not limited to Bluetooth (including BLE), any IEEE 802.11 wireless protocol and/or cellular protocols. RF communication circuits 754-1 can be connected to an antenna system 774.

In this way, a system can include a controller device with configurable analog circuits and/or configurable digital circuits. Such an arrangement can enable a common architecture to accommodate different sensors, and sensing types. For example, while FIG. 7 shows a radar IC device 702, alternate embodiments can include an optical (e.g., PPG) sensor or capacitance sensor, or combinations thereof. Signal paths and processing can be configured for such different sensors. Signal processing can be hardware accelerated with programmable digital circuits according to sensor type.

While FIG. 7 shows a system that can advantageously include programmable analog and digital circuits, alternate embodiments can include such functions as fixed function circuits in one or more ICs.

FIG. 8A-0 is a diagram showing a sensor system 800 according to a further embodiment. A system 800 can include a biophysical sensor 802, a capacitance sensor 804 and a controller 806. In some embodiments, a controller 806 can be part of the biophysical sensor 802 or the capacitance sensor 804. In other embodiments, a controller can be separate and remote from biophysical sensor 802 and capacitance sensor 804.

A biophysical sensor 802 and a capacitance sensor 804 can be mounted on a same sensor structure 816. That is, system 800 can be a "fusion" of two or more sensors. A biophysical sensor 802 and a capacitance sensor 804 can take the form of any of those shown herein and equivalents. A sensor structure 816 can take any suitable form, including a flat shape or a curved shape, such as one that can conform to a body surface. Sensor structure 816 can orient sensors to face a surface of a body 876. For example, radar antennas, light emitters and light sensors, and capacitance arrays can be arranged to face a body surface.

In some embodiments, a portion of a sensor structure 816 can include a circuit board to provide communication paths between a controller 806 and the sensors (802 and 804). However, alternate embodiments can include either or both sensors (802 and 804) being in wireless communication with a controller 806.

In the embodiment shown, a system 800 can be physically attached to a surface of a body 876 (which in the embodiment shown can be a limb). Further, system 800 can sense a structure of a circulatory system, such as an artery 878. System 800 can be positioned with biophysical sensor 802 proximate to the sensed structure 878. Capacitance sensor 804 can sense movement of the body 876. If such movement is sensed, biophysical sensor 802 can be placed into a sleep mode. When the body 876 is determined to be still by operation of capacitance sensor 804, biophysical sensor 802 can be placed into a sense mode, and can take sensor readings of sensed structure 878 or such sensor readings can be considered valid (with sensor readings being invalid when not still).

FIG. 8A-1 is a diagram showing a sensor system 800 in another orientation. FIG. 8A-1 shows how a capacitance sensor 804 for motion can be offset from the feature to be sensed (e.g., artery 878).

FIGS. 8B-0 and 8B-1 are a side and top views of a sensor system 800 like that of FIG. 8A. As shown in FIG. 8B-1, a capacitance sensor 804 can take various forms including a single capacitance sensor 804-0 or an array of capacitance sensors 804-1.In some embodiments, a system 800 can include a power source, such as a battery for portability.

In this way, a sensor system 800 can be fusion sensor with more than one sensor in a same structure, for a compact device that can be easily placed on a body.

FIG. 9A is a diagram showing a sensor system 900A according to another embodiment. A system 900A can include a biophysical sensor 902 that is separate from a capacitance sensor 904. In some embodiments, a controller 906 can be part of the biophysical sensor 902 or the capacitance sensor 904. In other embodiments, a controller can be separate and remote from sensor (902 and 904). In some embodiments, a communication path 920 can exist between biophysical sensor 902 and capacitance sensor 904.

Capacitance sensor 904 can be located close enough to biophysical sensor 902 to sense body movement that could affect readings of biophysical sensor 902. If movement is sensed, biophysical sensor 902 can be placed into a sleep mode. If movement is not sensed, biophysical sensor 902 can be placed into a sense mode. Such mode switching can be in response to a controller located on capacitance sensor 904, a controller located on the biophysical sensor 902, or a remote controller in communication with capacitance sensor 904.

In this way, a capacitance sensor that is separate from a biophysical sensor can control operations of the biophysical sensor based on detected motion. Such an arrangement can enable a biophysical sensor to be moved or adjusted while a capacitance sensor can remain in place.

FIG. 9B shows how a sensor system 900B can be positioned next to, rather than over, a sensed feature 878 (e.g., artery). As but one example, radar sensors may be capable of sensing features not directly below a sensor.

FIGS. 10A and 10B are diagrams showing wearable systems 1000A and 1000B according to embodiments. FIGS. 10A and 10B shows systems 1000A/B that can sense a body feature1078, such as an artery.

FIG. 10A shows a system 1000A that includes sensors/controller 1002/4/6 and a body attachment mechanism 1080A. Sensors/controller 1002/4/6 can include a combination of a biophysical sensor, capacitance sensor for detecting motion, and a controller for controlling the biophysical sensor as described herein and equivalents. Attachment mechanism 1080A can position sensors/controller 1002/4/6 proximate a sensed feature 1078 (e.g., artery) of a body 1076. In the embodiment shown, attachment mechanism 1080A can be a band.

FIG. 10B a system 1000B like that of FIG. 10A, but attachment mechanism 1080B for sensor/controller 1002/4/6 can include an adhesive or the like.

In this way, systems can be wearable devices, enabling a monitored subject to move about as desired, with biophysical readings being automatically taken when the subject is still. Such control of sensing operations can conserve power, enabling such systems to be worn for relatively long periods of time between charging.

Figures 11A, 11B, 11C, 11D:
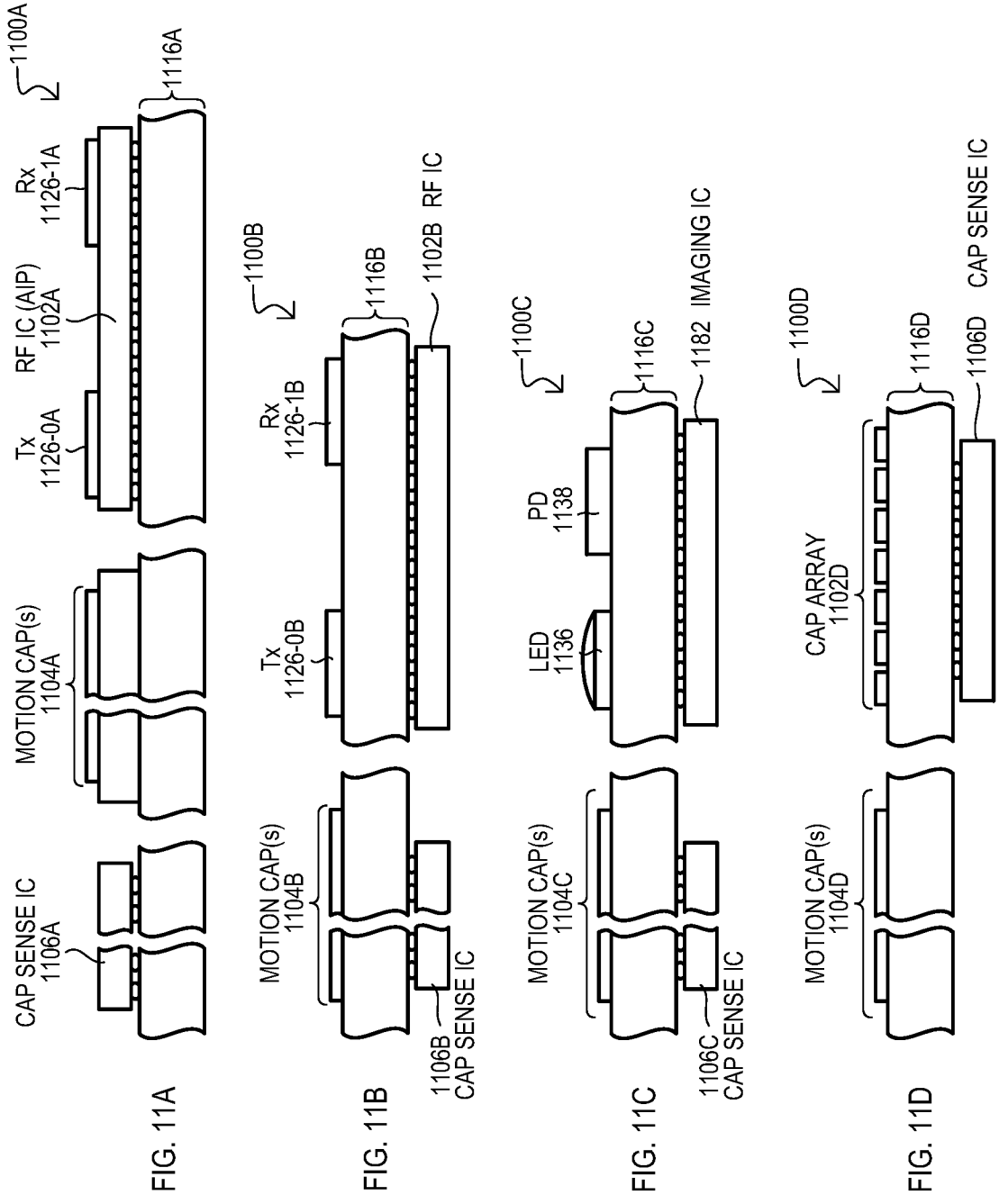
FIGS. 11A to 11D are side partial cross sectional views of systems according to embodiments.

FIGS. 11A to 11D are partial side cross sectional views of systems according to various embodiments. FIG. 11A shows a system 1100A that includes an RF IC 1102A, a motion capacitance sensor 1104A, and a cap sense IC 1106A mounted to a sensor structure 1116A. An RF IC 1102A can be an antenna-in-package (AIP) device that includes one or more Rx antennas and one or more Tx antennas (1126-0A, 1126-1A) on the IC package. RF IC 1102A can be switched between sense and sleep modes in response to movement detected by capacitance sensor 1104A, as described herein and equivalents.

Motion capacitance sensor 1104A can include one or more capacitance sensing electrodes for sensing motion as described herein and equivalents. A cap sense IC 1106A can be in communication with motion capacitance sensor 1104A, and can generate a motion detection indication as described herein. In some embodiments, cap sense IC 1106A can include a controller, which can place RF IC 1102A into sleep and sense modes. In other embodiments, an RF IC 1102A can include a controller. In still other embodiments, a controller can be an IC different from the RF IC 1102A and cap sense IC 1104A (e.g., a microcontroller, SoC, etc.).

A sensor structure 1116A can provide a structure for mounting the system components (1102A, 1104A, 1106A). In some embodiments, sensor structure 1116A can include a circuit board that provides conductive paths between the system components (1102A, 1104A, 1106A). While system 1100A shows cap sense IC 1106A mounted on a same side as RF IC 1102A and motion capacitance sensor 1104A, in other embodiments cap sense IC 1106A can be mounted on an opposing side of structure 1116A. In some embodiments, a sensor structure can include a portable power source, such as a battery or supercapacitor. A sensor structure 1116A can also includes physical features (e.g., edges or walls) that can ensure sensors components (1104A, 1102A) are positioned at a desired distance from a sensed surface (e.g., skin). A sensor structure 1116A can also include other layers, such as dielectric layers over electrodes.

FIG. 11B shows a system 1100B like that of FIG. 11A, but with an RF IC 1102B that is not an AIP type device. As a result, Rx and Tx antennas (two shown as 1126-0B, 1126-1B) can be mounted on surface of structure 1116B. In the embodiment shown, Rx and Tx antennas (1126-0B, 1126-1B) and motion capacitance sensor 1104B can be mounted on one side of structure 1102B, while RF IC 1102B and cap sense IC 1106B can be mounted on an opposing side of structure 1116B.

FIG. 11C shows a system 11000 like that of FIG. 11B, but with an optical sensor as opposed to a radar sensor (e.g., radar IC). An optical sensor can include one or more light sources (one shown as LED 1136) and one or more photo-detectors (one shown as PD 1138). In some embodiments, a system 11000 can include an imaging IC 1182, which can process data from an optical sensor. Such data processing can include, but is not limited to PPG processing.

In the embodiment shown, light source(s) 1136, photo-detector(s) 1138 and motion capacitance sensor 1104C can be mounted on one side of structure 1116C, with cap sense IC 1106C and imaging IC 1182 mounted on an opposing side. However, alternate embodiments can have one or more such components mounted on the sensor side.

FIG. 11D shows a system 1100D like that of FIG. 11C, but with a capacitance sense array as a biophysical sensor as opposed to an optical sensor. In the embodiment shown, a cap sense IC 1106D can determine motion using motion capacitance sensor 1104D, and enable or disable sensing with capacitance sense array 1102D based on detected motion. However, alternate embodiments can include separate devices for controlling such sensing. Further, alternate embodiments can include one or more electrodes within capacitance sense array 1102D serving as a motion detection electrode, and a separate motion capacitance sensor 1104D may not be included.

Sensor readings from capacitance array 1102D can be used to generate any suitable biophysical feature of a body. In some embodiments, such a biophysical feature can include, but is not limited to: artery location, APW and artery dimensions. Artery dimensions can then be used to generate PTT and/or PWV values.

Figure 12:
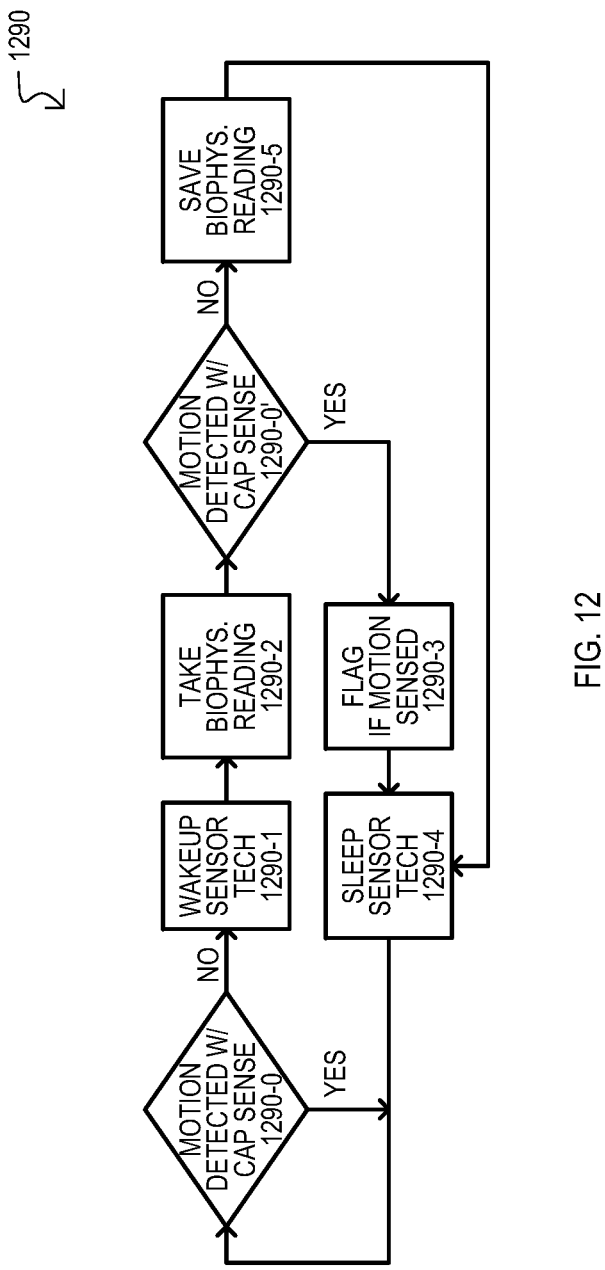
FIG. 12 is a flow diagram of a method according to an embodiment.

While the described devices and systems have disclosed various methods according to embodiments, additional methods will now be described with reference to flow diagrams. FIG. 12 is a flow diagram of a method 1290 according to an embodiment. A method 1290 can be executed by sensor systems disclosed herein and equivalents. A method 1290 can include detecting motion with capacitance sensing 1290-0. Such an action can include any of those described herein. If motion is not detected (NO from 1290-0), a method 1490 can wakeup sensor technology 1290-1. Such an action can include enabling one or more biophysical sensors, including switching a biophysical sensor from a sleep mode to a sense mode. In some embodiments, such an action can include any of: enabling a radar sensor, an optical sensor and/or a capacitor array sensor. A biophysical reading can be taken 1290-2. Such an action can include any of those described herein or equivalents, including emitting radar waves and detecting reflected radar waves, emitting light and detecting reflected light, or sensing changes in capacitance over an array of capacitance sensors. Such biophysical readings can include, or be used to generate, an artery location, APW, or artery dimensions.

A method 1290 can continue to detect motion with capacitance sensing 1290-0'. If motion is detected (YES from 1290-0'), a method 1290 can generate an indication (e.g., flag) that motion has been sensed 1290-3. Such an action can include any suitable action for a given system, including but not limited to: transitioning a signal from one level to another level, generating an interrupt, or writing a value to a storage circuit, such as a status register. If a motion indication is generated (1290-3), a method 1290 can place sensor technology into a sleep mode 1290-4. Such an action can include disabling one or more biophysical sensors, including switching a biophysical sensor from a sense mode to a sleep mode. In some embodiments, such an action can include placing sensor technology into a lower power consumption state. In other embodiments, such an action can include discarding or ignoring sensor readings. In still other embodiments, such an action can include increasing signal processing to account for the motion. A method 1290 can continue to monitor for motion (return to 1290-0).

If biophysical readings are taken and motion is not detected (NO from 1290-0'), a method 1290 can save a biophysical reading 1290-5. Such an action can include storing sensor data in storage circuits, including but not limited to: memory circuits, including volatile or nonvolatile memory circuits. Once sensor readings have been stored, a method 1290 can return a sensor to a sleep state (go to 1290-4).

In this way, a sensor system can stop sensing in the event sensor motion is detected, to prevent unwanted motion effects in sensor readings and saving system power for appropriate or optimal sensing conditions (e.g., still state).

Figure 13:
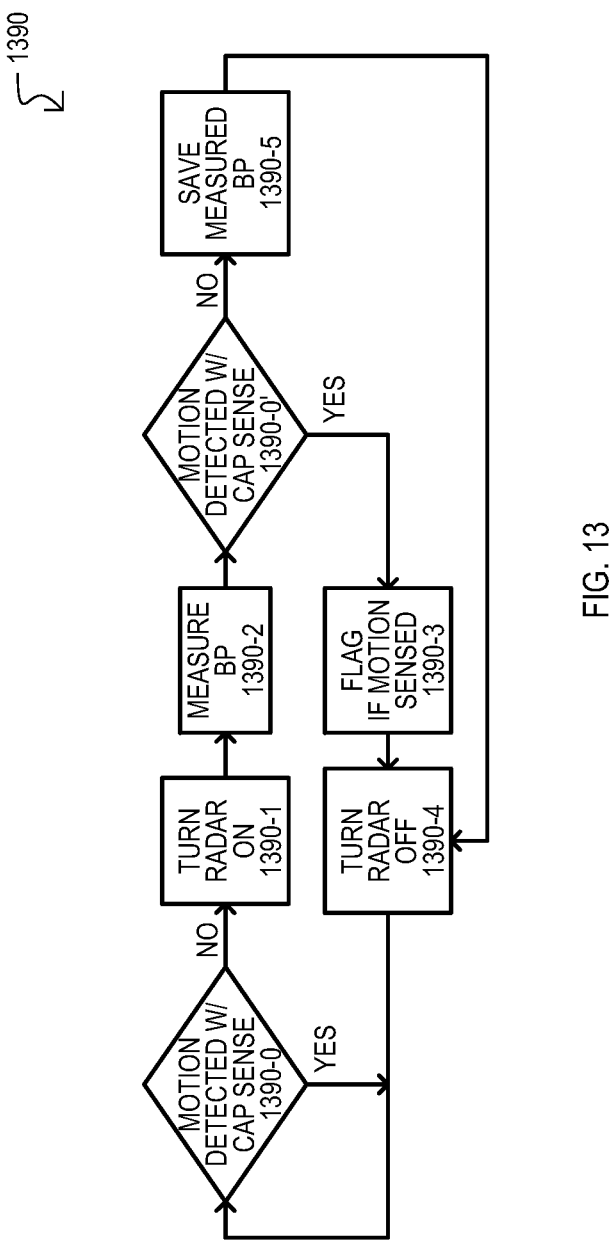
FIG. 13 is a flow diagram of a radar sensing method according to embodiments.

FIG. 13 is a flow diagram of a method 1390 according to another embodiment. A method 1390 can be executed by sensor systems having radar based biophysical sensors as disclosed herein and equivalents.

A method 1390 can include detecting motion with capacitance sensing 1390-0. Such an action can include any of those described herein. If motion is not detected (NO from 1390-0), a method 1390 can turn on radar of a sensor 1390-1. Such an action can include enabling radar transformers to power radar transmitters. In some embodiments, such an action can include transmitting radar signals of an AIP device. A method 1390 can take a biophysical measurement from such emitted radar 1390-2, which in the embodiment shown, can be a blood pressure related measurement. In some embodiments, such a measurement can be used to generate an APW.

A method 1390 can continue to detect motion with capacitance sensing 1390-0'. If motion is detected (YES from 1390-0'), a method 1390 can generate an indication (e.g., flag) that motion has been sensed 1390-3. If a motion indication is generated (1390-3), a method 1390 can turn radar off 1390-4. Such an action can prevent a radar reading from being taken while a sensed body is moving, which can introduce motion artifacts. This can also provide substantial reductions in power, enabling radar sensing to be introduced into low power applications, such as wearable devices and the like.

If motion is not detected (NO from 1390-0'), a method 1390 can save a blood pressure reading 1390-5.

Figure 14:
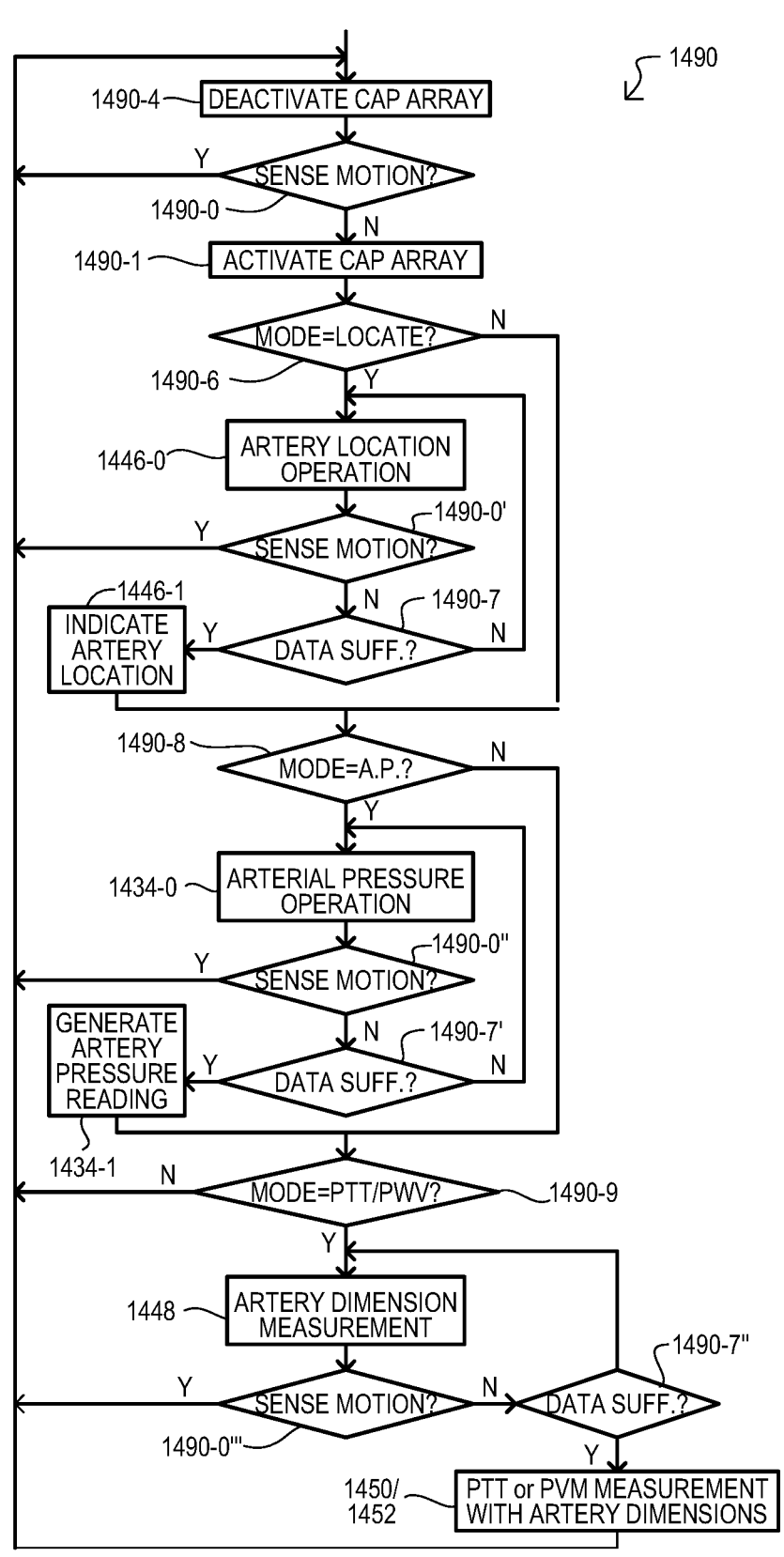
FIG. 14 is a flow diagram of a sensing method according to a further embodiment.

FIG. 14 is a flow diagram of a method 1490 according to a further embodiment. A method 1490 can include using a capacitance sense array (or other sensor technology) to perform any number of different sensing operations.

A method 1490 can include deactivating a capacitance sense array 1490-4. In some embodiments, this can include isolating capacitance electrodes, and deactivating capacitance sensing circuits. In some embodiments, this can include placing capacitance sense array and circuits into a sleep mode.

A method 1490 can sense for motion 1490-0. Such an action can include sensing with a capacitance sensor different from the deactivated capacitance sense array. However, in other embodiments, such an action can include using one or more electrodes of the capacitance sense array to sense motion. If motion is sensed (Y from 1490-0), a method 1490 can continue to deactivate the capacitance sense array 1490-4. If motion is not sensed (N from 1490-0), a method 1490 can activate a capacitance sense array 1490-1.

With a capacitance array activated 1490-1, a method 1490 can determine which particular sense mode of operation is being executed. If a mode is an artery location mode (Y from 1490-6), a method 1490 execute an artery location operation 1446-0. Such an action can include driving a capacitance sense array to determine a location of an artery. In some embodiments, artery location can include activating one or more indicators of a sensor device, including a visual indication or audio indication. While such readings are being taken, a method 1490 can continue to sense for motion 1490-0'. If motion is sensed (Y from 1490-0'), a method 1490 can deactivate the capacitance array 1490-4. While motion is not sensed (N from 1490-0'), a method 1490 can determine if sufficient sensor data has been acquired 1490-7. If sufficient data has not been acquired (N from 1490-7), the operation can continue. When sufficient data has been acquired (Y from 1490-7), an arterial location can be indicated (1446-1). Such an action can include any suitable indication as described herein and equivalents.

If a mode is an arterial pressure mode (Y from 1490-8), a method 1490 can execute an arterial pressure measurement operation 1434-0. Such an action can include driving a capacitance sense array to sense arterial pressure 1434-0. While such readings are being taken, if motion is sensed (Y from 1490-0"), a method 1490 can deactivate the capacitance array 1490-4. While motion is not sensed (N from 1490-0"), a method 1490 can determine if sufficient sensor data has been acquired 1490-7'. If sufficient data has not been acquired (N from 1490-7), the operation can continue. When sufficient data has been acquired (Y from 1490-7'), an arterial pressure reading can be generated (1434-1). Such an action can include any suitable indication as described herein and equivalents, including but not limited to blood pressure and/or an APW.

If a mode is an arterial dimension mode (Y from 1490-9), a method 1490 execute an arterial dimension measurement operation 1448. Such an action can include driving a capacitance sense array to measure arterial dimensions. While such readings are being taken, if motion is sensed (Y from 1490-0'''), a method 1490 can deactivate the capacitance array 1490-4. While motion is not sensed (N from 1490-0'''), a method 1490 can acquire sensor data until sufficient data has been acquired for a reading (Y from 1490-7"). When sufficient data has been acquired (Y from 1490-7"), arterial measurements can be used to generate PTT values and/or PVM values.

While FIG. 14 discloses a sense array for generating measurements in various modes, alternate embodiments can use different sensor types for such different modes. Including mixing sensing mode types (e.g., radar for arterial pressure, capacitance sensing for artery dimensions).

Embodiments can include any suitable capacitance sensing methods for detecting movement of a body. FIGS. 15A and 15B are diagrams showing a sensor system 1500 that can utilize self-capacitance to detect movement. FIG. 15A is a side cross sectional view of a system 1500. FIG. 15B is a top plan view of a system 1500. A system 1500 can include at least one capacitance sense (cap sense) electrode 1504 and a biophysical sensor array 1502. A cap sense electrode 1504 can be in proximity to sensed body 1576 that includes a sensed feature 1578. A biophysical sensor array 1502 can generate readings for sensed feature 1578.

With cap sense electrode 1504, a self-capacitance (Csense) can be measured with respect to sensed body 1576. In the event cap sense electrode 1504 moves with respect to the sensed body 1576, Csense can change, indicating movement. As but one example, as cap sense electrode 1504 moves further away from body 1576 Csense may decrease. As cap sense electrode 1504 moves further toward body 1576 Csense may increase. If Csense varies by a predetermined amount, motion can be detected.

FIG. 15C shows various sensor configurations according to embodiments. FIG. 15C shows a system 15000 that includes a biophysical sensing subsystem 1508, a motion sensing subsystem 1510, and a sensor structure 1516. A sensor structure 1516 can include one or more electrodes and/or electrode arrays 1502/1504.

A biophysical sensing subsystem 1508 can sense a biophysical feature, such as radar used to derive an APW. A motion sensing subsystem 1510 can sense motion events, and in response generate a motion event indication 1509. In response to a motion event indication 1509, a biophysical sensing subsystem 1508 can control sensing of a biophysical feature and/or the validity of data for a biophysical feature.

While embodiments can include separate sensors for sensing movement and biophysical features, alternate embodiments can include motion sensing subsystems 1510 that can receive data from biophysical sensor 1502 to detect motion (i.e., biophysical sensor 1502 can operate as a motion sensor, and electrode(s) 1504 may not be included). In such embodiments, data 1507 received by biophysical sensing subsystem 1508 can be forwarded to motion sensing subsystem 1510 to sense motion.

According to embodiments, systems can include electrode arrays having one or more electrodes that can operate in both motion sensing and biophysical feature sensing. FIGS. 16A to 16C are diagrams showing systems with multi-purpose electrodes according to embodiments.

FIG. 16A is a side cross sectional view of a system 1600 according to embodiments. A system 1600 can include a sensor array 1644A that includes one or more shared electrodes 1625 and one or more unshared electrodes 1626. A shared electrode 1625 can be used to both sense movement of a body 1676 and to sense a feature 1678 of the body. Unshared electrodes 1626 can be used for sensing feature 1678, but not motion sensing.

FIG. 16B is a block diagram of a system 1600B according to an embodiment. A system 1600B can include a sensor array 1644B that includes a shared electrode 1625 and unshared electrodes 1626. By operation of a switching circuit 1613B, a shared electrode 1625 can be selectively connected to a motion sensing subsystem 1610 or a biophysical sensing system 1608B according to a mode signal Mode.

FIG. 16C is a block diagram of a system 16000 according to another embodiment. A system 16000 can include a sensor array 1644C array. By operation of a switching circuit 1613C, a shared electrode 1625 can be selectively connected to a motion sensing subsystem 1610 or to a radar sensing subsystem 1608C, which senses a biophysical structure (e.g., artery). In the embodiment shown, a shared electrode 1625 can serve as a ground electrode 1611 in the radar sensing subsystem 1608C.

While embodiments have shown electrode arrays with same size electrodes arranged in a regular array, such configurations should not be construed as limiting. Embodiments can include electrode arrays with different sized electrodes of any suitable configuration.

FIG. 17 shows a system 1700 that can sense the motion of a body 1776 and can also sense a feature 1778 of the body. A system 1700 can include an electrode array 1744 having a motion sensing electrode 1704 that surrounds an array of biophysical feature sensors (two shown as 1726). In some embodiments, motion sensing electrode 1704 can be used to sense motion by measuring a self-capacitance. Array 1744 can be any suitable sensor array of electrodes, including a capacitance sensor array and/or a radar sensor array FIGS. 18A and 18B are diagrams showing a system 1800 and operations according to another embodiment. Referring to FIG. 18A, a system 1800 can include an electrode array 1844 having a motion sensing electrode 1804 surrounded by feature sensing electrodes (three shown as 1826). In some embodiments, motion sensing electrode 1804 can sense motion with self-capacitance. However, in other embodiments, motion sensing electrode 1804 can sense a mutual capacitance with one or more other electrodes of the electrode array 1844. Array 1844 can be any suitable sensor array of electrodes, including a capacitive sensor and/or radar sensor.

FIG. 18B is a timing diagram showing an example of sensing operations for a system like that shown in FIG. 18A. A shared electrode 1804 can be used for motion sensing. If such motion sensing indicates no motion (still) 1827-0, shared and unshared electrodes (1804/1826) can execute a feature sensing operation 1827-1. In alternate embodiments, an electrode 1804 may not be a shared electrode and not be used on a feature sensing operation 1827-1. If such motion sensing indicates motion (Movement) 1827-2, no feature sensing operation can occur.

As noted herein, while embodiments can include self-capacitance to detect movement other suitable methods can include mutual capacitance sensing. Mutual capacitance sensing can detect a change in capacitance between two electrodes. FIGS. 19A and 19B are diagrams showing mutual capacitance sensing system 1900 that can be included in embodiments. A system 1900 can include multiple electrodes (two shown as 1904-0/1), a driver 1931, and a dielectric 1929. An electrode (e.g., 1904-0) can be driven, and a capacitance Cmut between the driven electrode and another electrode (e.g., 1904-1) can be measured (by capacitance sensing circuits not shown). A change in the proximity of a sensed body 1976 (i.e., d1 to d2) can result in a change in mutual capacitance (from Cmut to Cmut'), thus detecting motion of the body.

In some embodiments, movements of a sensed body can be detected by changes in orientation (e.g., "tilt") of the sensor device with respect to a sensed body. In some embodiments, such changes can be sensed by two or more capacitance sensors spaced apart from one another. As a body moves, there can be a change in the orientation of the sensor with respect to the sensor device (or vice versa). Such a change in orientation can result in changes in capacitance at the capacitance sensors. FIGS. 20 to 22 show a three of many possible embodiments based on this approach.

FIG. 20 is a side cross sectional view of a system 2000 according to an embodiment. A system 2000 can include two or more cap sense electrodes 2004-0 and 2004-1 spaced apart from one another. In the embodiment shown, cap sense electrodes 2004-0/1 can be positioned at the edges of feature sensing electrodes 2026. Feature sensing electrodes 2026 can sense a feature 2078 of a sensed body 2076. When a sensed body 2076 is still, a capacitance measured by each cap sense electrode (Csense1, Csense2) can have a set value that remains the same, or remains within a predetermined range. When a sensed body 2076 moves, capacitance Csense1 and/or Csense2 can change, as one or both edges of the system 2000 may move closer or further away from the sensed body 2076. Such changes in capacitance can indicate movement, and result in any of: stopping the sensing by the feature sensing electrodes 2026, invalidation of the sensor readings generated by the sensing electrodes 2026, or flagging sensor readings generated by the sensing electrodes 2026 as corresponding to movement, and thus subject to additional processing.

FIG. 21 shows a system 2100 according to another embodiment that can be one implementation of that shown in FIG. 20. A system 2100 can include a sensor array 2144 having an array of first electrodes (one shown as 2126) surrounded by second electrodes 2104-0 to -3. In some embodiments, second electrodes 2104-0 to -3 can be cap sense electrodes for motion sensing, detecting changes in orientation of the system 2100 with respect to a sensed body 2176. First electrodes 2126 can sense a feature 2178 of the sensed body. In some embodiments, second electrodes 2104-0 to -03 can serve only as motion sensing electrodes. However, in other embodiments, second electrodes 2104-0 to -03 can also serve as feature sensing electrodes (i.e., can work in conjunction with electrodes 2126.

FIG. 22 shows a system 2200 according to an embodiment that can be one implementation of that shown in FIG. 20. A system 2200 can include first electrodes (one shown as 2226) and second electrodes 2204-0 to -3 organized into a regular sensor array 2244. Second electrodes 2204-0 to -03 can be those electrodes at the edge (e.g., corners) of the array 2244, and can be cap sense electrodes for motion sensing of sensed body 2276. First electrodes 2026 can sense a feature 2278 of the sensed body. As in the case of other embodiments, second electrodes 2204-0 to -03 can also serve as feature sensing electrodes (i.e., can work in conjunction with electrodes 2226) when sensing features 2278.

Embodiments can include electrode arrangements of any variety or number suitable to the sensing operations being performed. As but one of many possible examples, FIG. 23 shows a radar sensor array 2344 that can be included in embodiments having one transmitting electrode 2326-0 and multiple (in this embodiment three) receiving electrodes 2326-1. While receiving electrodes 2326-1 are shown in one particular orientation, alternate embodiments can include other orientations.

Embodiments can include electrode shapes of any shape or orientation suitable for the sensing operation being performed. As but one of many possible examples, FIG. 24 shows a sensor array 2444 having electrodes 2426 with elongated shapes that can be included in embodiments. As understood from the description herein, alternate embodi-ments can include electrodes of other shapes, including irregular shapes, and arrays with electrodes having different shapes from one another.

Figure 25:
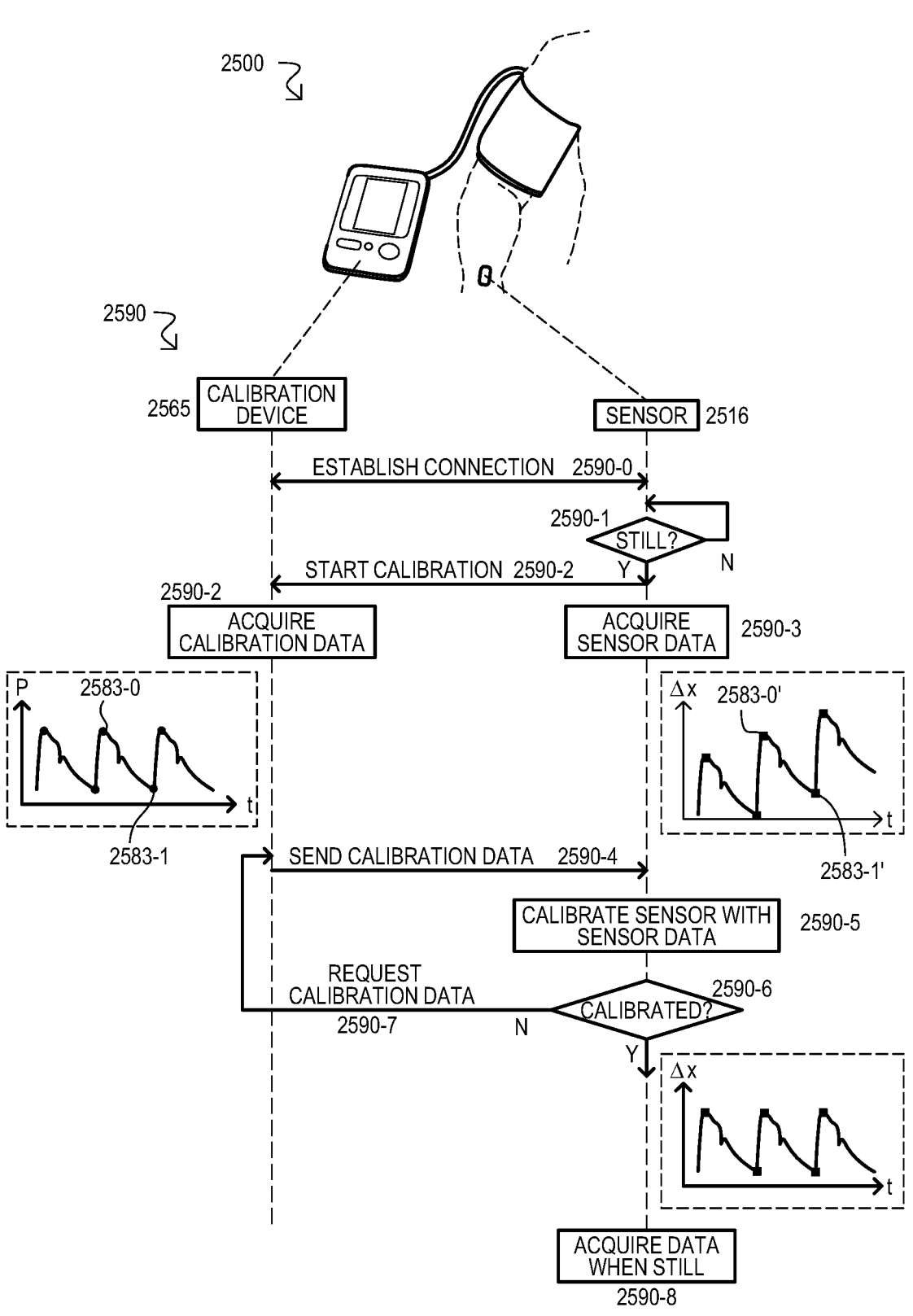
FIG. 25 is a diagram showing a system and method for calibrating a sensor system according to an embodiment.

While embodiments can include sensor systems that can be positioned on a body to control the sensing one or more biophysical features in response to body motion, embodiments can also include calibration operations for such systems. Some sensor systems may provide readings that can initially vary between application, such variance can result from factors including but not limited to: sensor orientation, sensor position, location on body, or subject physiology. Accordingly, a sensor system can benefit from an initial calibration with calibrating device. FIG. 25 shows a calibration system 2500 and method 2590 according to one embodiment.

A calibration system 2500 can include a sensor device 2516 and a calibration device 2565. A sensor device 2516 can take the form of any of those described herein, or an equivalent. A calibration device 2565 can sense the same, or corresponding biological feature as the sensor device 2516, but may provide initial results that can be more accurate than sensor device 2516, when the sensor device 2516 is uncalibrated. A calibration device 2565 and sensor device 2516 can be in communication with one another over any suitable connection, including a wired or wireless connection.

In one embodiment, a calibration device 2565 can be a sphygmomanometer, and a sensor device 2516 can be a APW sensor, that utilizes capacitance, radar and/or PPG to generate an APW.

Referring still to FIG. 25, a method 2590 can include establishing a connection 2590-0 between the calibration device 2565 and the sensor device 2516. Once a sensor device determines the sensed body is still (Y from 2590-1), a calibration operation can start 2590-2. Such an action can include a calibration device acquiring calibration data 2590-2, and the sensor device acquiring sensor data 2590-3. In some embodiments, such an action can include calibration device 2656 and sensor device 2516 acquiring data over a same time period. Calibration data can provide values for adjusting how sensor device 2516 acquires sensor data. In some embodiments, calibration data can indicate particular points in a waveform corresponding to a feature. In one embodiment, calibration data can be for a blood pressure waveform, and can indicate a systolic peak 2583-0 and well as a diastolic pressure end 2583-1.

Sensor data acquired in 2590-3 can result in an initial waveform that varies from a desired waveform. In one embodiment, sensor data can be for an APW, and can sense a systolic peak 2583-0' and well as a diastolic pressure end 2583-1'. However, such initial data points may be offset from a desired waveform.

A method 2590 can include a calibration device 2565 sending calibration data to a sensor device 2590-4. From calibration data, a sensor device can perform a calibration operation 2590-5 that can adjust how sensor data is generated. In one embodiment, a calibration data can indicate corresponding points in sensor data, enabling a sensor device 2516 to a function and/or offset to arrive at desired sensor results.

If calibration is not successful (N from 2590-6), a sensor device can request more calibration data 2590-7. If calibration is successful (Y from 2590-6), a sensor 20 device can generate sensor data based on whether the subject is still 2590-8 as described herein and equivalents. A sensor device 2516 can then disconnect from calibration device 2565.

Figure 26:
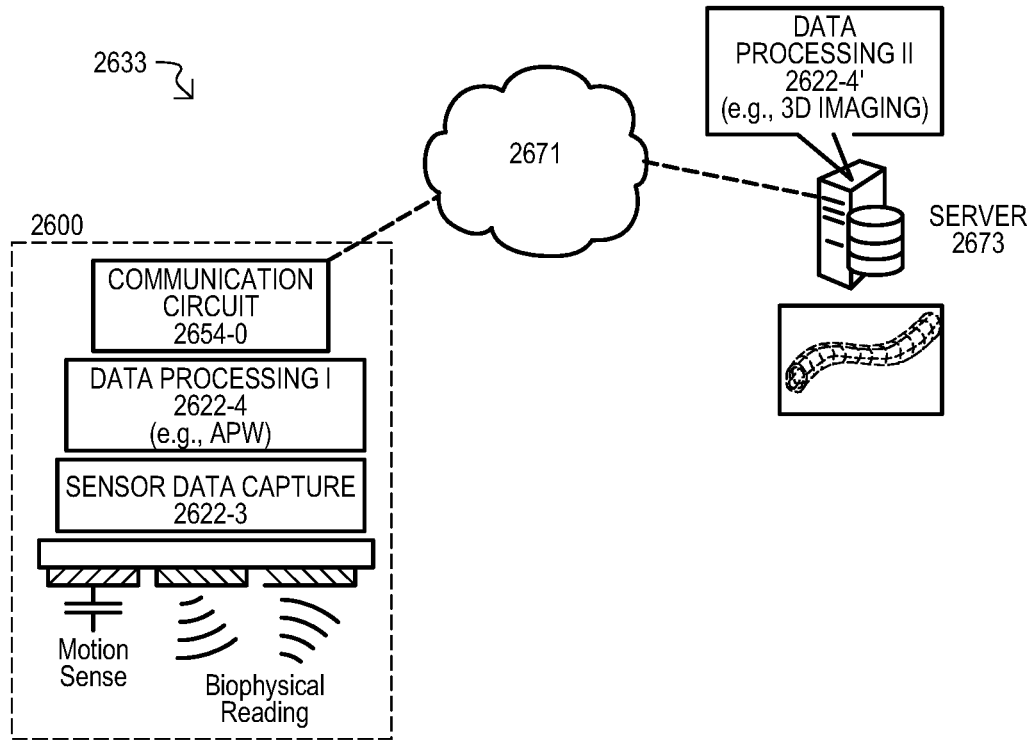
FIG. 26 is a diagram of a sensor system according to a further embodiment.

While embodiments can include sensor devices that generate a desired biophysical reading, in some embodiments, sensor devices can operate in conjunction with greater computing resources to generate a desired biophysical reading and/or additional biophysical readings. FIG. 26 shows a sensing system 2633 according to such an embodiment. A sensing system 2633 can include a sensor device 2600 as described herein, or an equivalent. A sensor device 2600 can provide motion sensing as well as the sensing of one or more biophysical features. Sensor data can be captured 2622-3. In some embodiments, captured sensor data can be subject to data processing 2622-4 to generate some initial sensing results. In one embodiment, sensor data can be processed locally by a sensor device 2600 to generate an APW. A sensor device 2600 can include communication circuits 2654-0 that can transmit sensor readings to high resource system 2673 over a communications network 2671. Such transmitted sensor readings can be raw sensor readings, processed sensor readings, or combinations thereof. Due to communications network 2671, high resource system 2673 can be local to a sensor device 2600 or remote from sensor device 2600. In some embodiments, a high resource system 2673 can be a server system.

High resource system 2673 can have greater computing resources that sensor device 2600. High resource system 2673 can perform data processing on sensor readings to generate biophysical result. Such a biophysical result can be different from that generated by sensor system 2673. In one embodiment, data processing 2622-4 of sensor device 2600 can generate an APW, while data processing 2622-4' by high resource system 2673 can generate any of: a higher resolution APW (than that of sensor device 2600), dimensions of an artery (including three-dimensional images), and 3D imaging that shows changes in artery shape over time.

Embodiments can include a method in which a sensor device contained in a sensor structure is attached to a body, a motion of the body is sensed with at least one motion capacitive sensor of the sensor device. The motion capacitive sensor senses a capacitance change resulting from a difference in orientation of the motion capacitive sensor and a surface of the body. If motion of the body is not sensed with the motion capacitive sensor, sensor readings can be acquired with a biophysical sensor that emits signals into a portion of the body below the sensor structure, and data can be generated for a feature of the body with the sensor readings. If motion of the body is sensed with the motion capacitive sensor, data for the feature of the body is not generated.

Embodiments can include a device having a sensor structure configured to be attached to a body; a motion capacitive sensor attached to the sensor structure and configured to activate a motion indication in response to capacitance changes resulting from a difference in orientation of the motion capacitive sensor and a surface of the body; a biophysical sensor configured to be attached to the body and configured to in response to the motion indication being inactive, acquire sensor readings with a biophysical sensor that emits signals into a portion of the body below the sensor structure, and generate data for a feature of the body with the sensor readings; and in response to the motion indication being active, not generate data for a feature of the body with the sensor readings.

Embodiments can include a system having a motion capacitive sensor configured to attach to a body and to sense motion of the body by detecting capacitance changes resulting from a difference in orientation of the motion capacitive sensor and a surface of the body; and a biophysical sensor configured to attach to the body and configured to if motion of the body is not sensed with the motion capacitive sensor, acquiring sensor readings with a biophysical sensor that emits signals into a portion of the body below the sensor structure, and generate data for a feature of the body with the sensor readings; and if motion of the body is sensed with the motion capacitive sensor, not generate data for the feature of the body.

Methods, devices and systems according to embodiments can further measure a circulatory system feature of the body.

Methods, devices and systems according to embodiments can include an array of radar sensor electrodes. Taking sensor readings with the biophysical sensor can include emitting radar waves into the body and receiving reflected radar waves from the body.

Methods, devices and systems according to embodiments can include one or more one light emitting device and one or more light detecting device. Sensor readings can include emitting light at the body and detecting light reflected from the body.

Methods, devices and systems according to embodiments can include a biophysical sensor having an array of capacitance sensing electrodes. In some embodiments, one or more of the capacitance sensing electrodes can be part of the motion capacitive sensor. In other embodiments, one or more capacitance sensing electrodes can be different from the array of capacitance sensing electrodes.

Methods, devices and systems according to embodiments can include a biophysical sensor having an array of radar sensing electrodes. In some embodiments, one or more of the radar sensing electrodes can be part of the motion capacitive sensor. In other embodiments, one or more capacitance sensing electrodes can be different from the array of radar sensing electrodes.

Methods, devices and systems according to embodiments can include a motion capacitive sensor that measures self-capacitance of one or more electrodes to detect motion.

Methods, devices and systems according to embodiments can include a motion capacitive sensor that measures mutual capacitance between two or more electrodes to detect motion.

Methods, devices and systems according to embodiments can include disabling sensor readings of a biophysical sensor in response to a motion indication generated by a motion capacitive sensor to reduce power consumption.

Methods, devices and systems according to embodiments can include a biophysical sensor that is a radar sensing having one or more transmitting antennas and one or more receiving antennas.

Methods, devices and systems according to embodiments can include a biophysical sensor attached to a same sensor structure as a motion capacitive sensor.

Methods, devices and systems according to embodiments can include a motion capacitive sensor with one or more motion sense electrodes configured to be disposed above the surface of the body when the sensor structure is attached to the body. A biophysical sensor can include a plurality of electrodes configured to be disposed above the surface of the body.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claims require more features than are expressly recited in each claim. Rather, inventive aspects lie in less than all features of a single foregoing disclosed embodiment. Thus, the claims following the detailed description are hereby expressly incorporated into this detailed description, with each claim standing on its own as a separate embodiment of this invention.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method, comprising:
attaching a sensor device contained in a sensor structure to a body;
sensing motion of the body with at least one motion sense electrode of a motion capacitive sensor of the sensor device that senses a capacitance change resulting from a difference in orientation of the at least one motion sense electrode and a surface of the body;
if motion of the body is not sensed with the motion capacitive sensor,
acquiring sensor readings with a biophysical sensor having a plurality of sensor electrodes comprising an array of radar sensor electrodes, including at least one sensor electrode that emits radar wave signals into a portion of the body below the sensor structure and at least one other sensor electrode that receives reflected radar waves from the body, and
generating data for a feature of the body with the sensor readings; and
if motion of the body is sensed with the motion capacitive sensor, not generating data for the feature of the body.

2. The method of claim 1, wherein the feature is a circulatory system feature of the body.

3. The method of claim 1, wherein the at least one motion sensing electrode measures changes in a self-capacitance of the at least one motion sensing electrode.

4. The method of claim 1, wherein the at least one motion sensing electrode comprises at least two motion sensing electrodes that measure changes in mutual capacitance between at least two of the motion sensing electrodes.

5. A device, comprising:
a sensor structure configured to be attached to a body;
a motion capacitive sensor attached to the sensor structure and configured to activate a motion indication in response to capacitance changes resulting from a difference in orientation of at least one motion sense electrode of the motion capacitive sensor and a surface of the body, the at least one motion sense electrode configured to be disposed above the surface of the body when the sensor structure is attached to the body;

a biophysical sensor configured to be attached to the body that includes a plurality of sensor electrodes configured to be disposed above the surface of the body and configured to
in response to the motion indication being inactive,
acquire sensor readings with a biophysical sensor that emits signals into a portion of the body below the sensor structure, and
generate data for a feature of the body with the sensor readings; and
in response to the motion indication being active, not generate data for a feature of the body with the sensor readings; wherein
the biophysical sensor comprises a radar sensor that includes at least one sensor electrode configured as a transmitting antenna and at least one other sensor electrode configured as a receiving antenna.

6. The device of claim 5, wherein the biophysical sensor is configured to, in response to the motion indication being active, disable sensor readings to reduce power consumption.

7. The device of claim 5, wherein the biophysical sensor is attached to the sensor structure.

8. The device of claim 5, wherein:
the biophysical sensor comprises an array of electrodes; and
the at least one motion sense electrode is one of the electrodes in the array of electrodes.

9. The device of claim 5, wherein:
the biophysical sensor comprises an array of electrodes; and
the at least one motion sense electrode is different from the array of electrodes.

10. A system, comprising:
a motion capacitive sensor configured to attach to a body and to sense motion of the body by detecting capacitance changes resulting from a difference in orientation of at least one motion sense electrode of the motion capacitive sensor and a surface of the body, the at least one motion sense electrode configured to be disposed above the surface of the body when the sensor structure is attached to the body; and
a biophysical sensor configured to attach to the body that includes a plurality of sensor electrodes configured to be disposed above the surface of the body and configured to
if motion of the body is not sensed with the motion capacitive sensor,
acquire sensor readings with a biophysical sensor that emits signals into a portion of the body below the sensor structure, and
generate data for a feature of the body with the sensor readings; and
if motion of the body is sensed with the motion capacitive sensor, not generate data for the feature of the body; wherein
the biophysical sensor comprises an array of electrodes comprising a radar sensing array.

11. The system of claim 10, wherein the motion capacitive sensor is selected from the group consisting of: a self-capacitance sensor and a mutual capacitance sensor.

12. The system of claim 10, wherein:
the at least one motion sense electrode is one of the electrodes in the array of electrodes.

13. The system of claim 10, wherein:
the at least one motion sense electrode is different from the array of electrodes.

14. The system of claim 10, wherein the capacitance sensor and biophysical sensor are part of a same sensor structure.

* * * * *